(12) United States Patent  
Komistek

(10) Patent No.: US 9,668,745 B2
(45) Date of Patent: Jun. 6, 2017

(54) ANATOMICAL CONCENTRIC SPHERES THA

(75) Inventor: Richard D. Komistek, Knoxville, TN (US)

(73) Assignee: DEPUY IRELAND UNLIMITED COMPANY (IE)

( * ) Notice: Subject to any disclaimer, the term of this patent is extended or adjusted under 35 U.S.C. 154(b) by 1091 days.

(21) Appl. No.: 13/330,259

(22) Filed: Dec. 19, 2011

(65) Prior Publication Data

US 2013/0158557 A1   Jun. 20, 2013

(51) Int. Cl.
| | |
|---|---|
| *A61B 17/56* | (2006.01) |
| *A61F 2/32* | (2006.01) |
| *A61B 17/15* | (2006.01) |
| *A61B 17/17* | (2006.01) |
| *A61F 2/46* | (2006.01) |
| *A61F 2/30* | (2006.01) |

(52) U.S. Cl.
CPC .......... *A61B 17/15* (2013.01); *A61B 17/1746* (2013.01); *A61F 2/4684* (2013.01); *A61F 2/32* (2013.01); *A61F 2002/30578* (2013.01); *A61F 2002/4663* (2013.01); *A61F 2002/4687* (2013.01)

(58) Field of Classification Search
CPC . A61B 17/56; A61B 17/15; A61F 2/32; A61F 2/4684
USPC .................. 623/22.21–22.39; 606/89, 90, 91
See application file for complete search history.

(56) References Cited

U.S. PATENT DOCUMENTS

| | | |
|---|---|---|
| 3,510,883 A | 5/1970 | Cathcart |
| 3,656,184 A | 4/1972 | Chambers |
| 3,891,997 A | 7/1975 | Herbert et al. |
| 3,925,824 A | 12/1975 | Freeman et al. |
| 4,024,588 A | 5/1977 | Janssen et al. |
| 4,032,994 A | 7/1977 | Frey |
| 4,068,324 A | 1/1978 | Townley et al. |
| 4,318,191 A | 3/1982 | Tepic |
| 4,528,980 A | 7/1985 | Kenna |
| 4,532,660 A | 8/1985 | Field |
| 4,795,470 A | 1/1989 | Goymann et al. |
| 4,878,916 A | 11/1989 | Rhenter et al. |
| 4,911,723 A | 3/1990 | Menschik |

(Continued)

FOREIGN PATENT DOCUMENTS

| | | |
|---|---|---|
| CN | 1076104 A | 9/1993 |
| CN | 1596091 A | 3/2005 |

(Continued)

OTHER PUBLICATIONS

International Search Report and Written Opinion, International Application No. PCT/US2012/070607, Jun. 24, 2014, 6 pages.

(Continued)

*Primary Examiner* — Christopher Beccia
(74) *Attorney, Agent, or Firm* — Barnes & Thornburg LLP

(57) ABSTRACT

Devices and methods for identifying and maintaining the concentric spherical centers of a femur and acetabulum during revision or joint replacement surgery so that post surgery the anatomical spherical centers are maintained. Also disclosed are novel techniques and devices to project images onto an anatomical feature, such as exposed bone, to virtually fit trial prosthetic components, establish bone cut markings, and establishing the anatomical spherical center of a joint.

10 Claims, 25 Drawing Sheets

(56) References Cited

U.S. PATENT DOCUMENTS

| | | |
|---|---|---|
| 4,955,919 A | 9/1990 | Pappas et al. |
| 4,960,427 A | 10/1990 | Noiles |
| 5,009,665 A | 4/1991 | Serbousek et al. |
| 5,047,062 A | 9/1991 | Pappas et al. |
| 5,326,368 A | 7/1994 | Collazo |
| 5,370,703 A | 12/1994 | Willert et al. |
| 5,431,657 A * | 7/1995 | Rohr ............................ 606/91 |
| 5,549,698 A | 8/1996 | Averill et al. |
| 5,553,476 A | 9/1996 | Oehy et al. |
| 5,593,447 A | 1/1997 | Angeli |
| 5,676,704 A | 10/1997 | Ries et al. |
| 5,702,474 A | 12/1997 | McCandliss |
| 5,824,108 A | 10/1998 | Huebner et al. |
| 5,879,405 A | 3/1999 | Ries et al. |
| 5,951,605 A | 9/1999 | Dennis et al. |
| 6,002,859 A | 12/1999 | DiGioia, III et al. |
| 6,066,176 A | 5/2000 | Oshida et al. |
| 6,093,208 A | 7/2000 | Tian et al. |
| 6,120,545 A | 9/2000 | Hamelijnck et al. |
| 6,126,695 A | 10/2000 | Semlitsch |
| 6,152,961 A | 11/2000 | Ostiguy, Jr. et al. |
| 6,197,032 B1 | 3/2001 | Lawes et al. |
| 6,200,350 B1 | 3/2001 | Masini |
| 6,206,929 B1 | 3/2001 | Ochoa et al. |
| 6,224,633 B1 | 5/2001 | Kalberer et al. |
| 6,248,132 B1 | 6/2001 | Harris |
| 6,416,553 B1 | 7/2002 | White et al. |
| 6,447,550 B1 | 9/2002 | Hunter et al. |
| 6,488,715 B1 | 12/2002 | Pope et al. |
| 6,503,281 B1 | 1/2003 | Mallory |
| 6,537,321 B1 | 3/2003 | Horber et al. |
| 6,641,617 B1 | 11/2003 | Merrill et al. |
| 6,682,566 B2 | 1/2004 | Draenert |
| 6,726,725 B2 | 4/2004 | Hunter et al. |
| 7,004,972 B2 | 2/2006 | Yoon |
| 7,044,974 B2 | 5/2006 | Garber et al. |
| 7,108,720 B2 | 9/2006 | Hanes |
| 7,179,296 B2 | 2/2007 | Dooney |
| 7,179,298 B2 | 2/2007 | Greenlee |
| 7,211,113 B2 | 5/2007 | Zelener et al. |
| 7,291,177 B2 | 11/2007 | Gibbs |
| 7,335,231 B2 | 2/2008 | McLean |
| 7,455,694 B2 | 11/2008 | Epaules et al. |
| 7,494,509 B1 | 2/2009 | Hershberger et al. |
| 7,572,296 B2 | 8/2009 | Scott et al. |
| 7,682,398 B2 | 3/2010 | Croxton et al. |
| 7,794,504 B2 | 9/2010 | Case |
| 7,985,261 B2 | 7/2011 | Masini |
| 8,177,850 B2 | 5/2012 | Rudan et al. |
| 8,211,183 B2 | 7/2012 | Podolsky |
| 8,211,184 B2 | 7/2012 | Ries et al. |
| 8,268,383 B2 | 9/2012 | Langhorn |
| 8,328,875 B2 | 12/2012 | Linares |
| 8,603,180 B2 | 12/2013 | White et al. |
| 2003/0212459 A1 * | 11/2003 | Gibbs ........................ 623/22.32 |
| 2003/0236572 A1 | 12/2003 | Bertram, III |
| 2004/0078083 A1 | 4/2004 | Gibbs et al. |
| 2004/0143341 A1 | 7/2004 | McLean |
| 2004/0193282 A1 | 9/2004 | Hanes |
| 2004/0204767 A1 | 10/2004 | Park et al. |
| 2004/0225371 A1 | 11/2004 | Roger |
| 2005/0096748 A1 | 5/2005 | Yoon |
| 2005/0107799 A1 | 5/2005 | Graf et al. |
| 2005/0261776 A1 | 11/2005 | Taylor |
| 2006/0058886 A1 | 3/2006 | Wozencroft |
| 2006/0167556 A1 | 7/2006 | Lazennec et al. |
| 2006/0206211 A1 | 9/2006 | Daniels et al. |
| 2006/0217815 A1 | 9/2006 | Gibbs et al. |
| 2007/0100447 A1 | 5/2007 | Steinberg |
| 2007/0106389 A1 | 5/2007 | Croxton et al. |
| 2007/0225818 A1 | 9/2007 | Reubelt et al. |
| 2008/0015707 A1 | 1/2008 | Lambert et al. |
| 2008/0114459 A1 | 5/2008 | Scott et al. |
| 2008/0177395 A1 | 7/2008 | Stinnette |
| 2008/0208350 A1 | 8/2008 | Roger |
| 2008/0294258 A1 | 11/2008 | Revie et al. |
| 2009/0018666 A1 | 1/2009 | Grundei et al. |
| 2009/0093887 A1 | 4/2009 | Walter et al. |
| 2009/0105714 A1 | 4/2009 | Kozak |
| 2009/0171464 A1 | 7/2009 | Imhof |
| 2009/0204225 A1 | 8/2009 | Meridew et al. |
| 2009/0259317 A1 | 10/2009 | Steinberg |
| 2009/0281545 A1 | 11/2009 | Stubbs |
| 2009/0287311 A1 | 11/2009 | Preuss et al. |
| 2011/0032184 A1 | 2/2011 | Roche et al. |
| 2011/0054628 A1 * | 3/2011 | Banks et al. ................ 623/22.19 |
| 2012/0029651 A1 | 2/2012 | Ashton et al. |
| 2012/0065737 A1 | 3/2012 | Chow |
| 2012/0109327 A1 | 5/2012 | Forsell |
| 2012/0209398 A1 | 8/2012 | Richardson et al. |
| 2012/0221115 A1 | 8/2012 | Komistek |
| 2013/0158557 A1 | 6/2013 | Komistek |
| 2013/0158674 A1 | 6/2013 | Chow et al. |
| 2013/0165938 A1 | 6/2013 | Chow et al. |
| 2013/0304225 A1 | 11/2013 | Komistek |

FOREIGN PATENT DOCUMENTS

| | | |
|---|---|---|
| CN | 1622790 A | 6/2005 |
| DE | 2139879 A1 | 2/1973 |
| DE | 3643815 A1 | 6/1988 |
| DE | 10212982 A1 | 10/2003 |
| EP | 524857 A1 | 1/1993 |
| EP | 0524857 A1 | 1/1993 |
| EP | 0649640 A2 | 4/1995 |
| EP | 0797964 A1 | 10/1997 |
| EP | 1508315 A2 | 2/2005 |
| EP | 1574183 A1 | 9/2005 |
| FR | 2785523 A1 | 5/2000 |
| FR | 2889446 A1 | 2/2007 |
| GB | 1573608 A | 8/1980 |
| RU | 2042345 C1 | 8/1995 |
| RU | 2116769 C1 | 8/1998 |
| WO | 9615735 A1 | 5/1996 |
| WO | 0064384 A1 | 11/2000 |
| WO | 0155476 A1 | 8/2001 |
| WO | 2008058756 A2 | 5/2008 |
| WO | 2009118673 A1 | 10/2009 |

OTHER PUBLICATIONS

International Search Report and Written Opinion, International Application No. PCT/US2013/040107, Dec. 6, 2013, 11 pages.
International Search Report and Written Opinion, International Application No. PCT/US2012/026492, Aug. 31, 2012, 5 pages.
International Search Report, International Application No. PCT/US2013/40107, Jun. 12, 2013, 11 pages.
International Search Report, International Application No. PCT/US2012/026492, Aug. 31, 2012, 16 pages.
Office Action and English Translation for Chinese Patent Application No. 201280070098.7, dated Oct. 8, 2016, 15 pages.

* cited by examiner

ANATOMICAL CONCENTRIC SPHERES THA

RELATED ART

Field of the Invention

The present invention generally relates to hip replacement and revision surgery, as well as associated structure and methods used to carry out the foregoing.

Background

Total hip arthroplasty (THA) is a surgical procedure that consists of replacing both the acetabulum and the femoral head. In contrast, hemiarthroplasty generally only replaces the femoral head. During THA, a surgeon makes an incision to directly access the patient's hip joint. The surgeon then dislocates the hip joint to separate the proximal end of the femur (including the femoral head) from the acetabulum. Without any point of reference other than experience, the surgeon makes a cut across the femur to remove the proximal end of the femur (including the femoral head and neck) and expose the intramedullary canal of the femur, which will be reamed or otherwise surgically prepared to accept a stem of a prosthetic femoral component. Likewise, without any reference point other than the location of the patient's natural acetabular cup, the surgeon reams the acetabulum to prepare the acetabulum to accept a prosthetic cup.

A significant problem resulting from THA is prosthetic ball and cup separation, whereas maximum contact area between the femoral head and the acetabular cup is not maintained. Most physicians and engineers refer to this as one of two clinical concerns: (1) femoral head separation; and, (2) the ball popping out of the cup socket leading to dislocation. When femoral head separation occurs, the femoral head slides out of the cup, mostly in the superolateral direction and the medial aspect of the femoral head is no longer in contact with the acetabular cup. This sliding phenomenon leads to shear forces and moments that were not present in the natural hip joint before surgery. When the ball pops into and out of the cup socket, shear forces and blunt impact forces are introduced between the components that are unintended and accordingly not accounted for in current prosthetic design. In a perfect world, the cup and socket would be in constant contact, maintaining maximum contact area with one another throughout a patient's entire range of motion of a hip joint, thereby significantly lessening shear forces and inhibiting blunt impact forces altogether.

As discussed in the present inventor's previous work, it is theorized that a majority of prosthetic ball and cup separation is the result of prosthetic components failing to replicate the natural biomechanics of the patient, most notably concentricity of the spheres. This may be the result of the design of the prosthetic components themselves or may also be the result of prosthetic components that are improperly implanted. More specifically, the present inventor has theorized that a patient's natural hip joint exhibits concentric spheres throughout motion. These concentric spheres are the spheres that result from picking a first sphere that best replicates the shape of the patient's proximal femoral head and picking a second sphere that best replicates the shape of the patient's acetabular cup. In a patient's natural hip joint, these spheres have the same center throughout motion. And the patient's soft tissue provides the necessary active forces and constraint forces to maintain this center post THA, whereas the geometry of the bones and the soft-tissues work together in unison. But this cannot happen if prosthetic THA components are implanted incorrectly or if implants are not designed with concentricity in mind. This also cannot happen using present day jigs, guides, and cutting instruments. Present day surgeons routinely cut the femoral head and ream the acetabulum without maintaining anatomical relationships with one another. Present day implants also do not allow for anatomical orientations as derived for specificity of subjects.

INTRODUCTION TO THE INVENTION

The present invention is directed to hip replacement and revision surgery, as well as associated structure and methods used to carry out the foregoing.

It is a first aspect of the present invention to provide a trial for use with total hip arthroplasty, the trial comprising a first spherical insert having a plurality of tabs mounted thereto, each of the plurality of tabs at least partially defining an orifice In a more detailed embodiment of the first aspect, the first spherical insert includes a first semispherical half and a second semispherical half that engage and disengage one another. In yet another more detailed embodiment, the first spherical insert is sized to fit within an unreamed acetabulum.

It is a second aspect of the present invention to provide a cutting guide for use with total hip arthroplasty, the cutting guide comprising a semispherical cutting guide for coupling to a proximal femur, the cutting guide including a concave section that mimics the arc of a natural femoral ball of a hip joint, the cutting guide including a retainer to fasten the cutting guide to the proximal femur.

In a more detailed embodiment of the second aspect, the retainer comprises a plate adapted to be adjacent an exterior of the proximal femur, the plate including at least one through orifice to receive a fastener. In yet another more detailed embodiment, the fastener includes at least one of a pin, a screw, a dowel, and a nail. In a further detailed embodiment, the retainer comprises at least two plates adapted to be adjacent an exterior of the proximal femur, at least one of the plates including at least one through orifice to receive a fastener.

It is a third aspect of the present invention to provide a guide for establishing the spherical center of a femoral ball, the guide comprising a plurality of plates repositionable with respect to one another to overly and collectively approximate to the circumferential curvature of a distal femoral head, wherein the plurality of plates are operative to retain this approximation of circumferential curvature after dismounted from the distal femoral head In a more detailed embodiment of the third aspect, at least one of the plurality of plates is deformable. In yet another more detailed embodiment, the plurality of plates are interconnected with one another using at least one line extending through orifices of the plurality of plates. In a further detailed embodiment, the plurality of plates comprise overlapping flights that fan out to circumscribe the distal femoral head.

It is a fourth aspect of the present invention to provide a guide set for use in a total arthroplasty procedure, the guide set comprising a plurality of guides adapted to interpose a human acetabulum and a human proximal femur, each of the guides including an acetabular cup mounted to a partial femoral component, the partial femoral component including an endplate adapted to contact at least one of an exterior of the human proximal femur and a portion of the human proximal femur not exposed prior to a bone cut.

In a more detailed embodiment of the fourth aspect, at least two of the plurality of guides each allows the partial femoral component to be repositioned with respect to acetabular cup mounted thereto. In yet another more detailed embodiment, at least two of the plurality of guides each does not allow the partial femoral component to be repositioned with respect to acetabular cup mounted thereto. In a further detailed embodiment, at least two of the plurality of guides each includes an endplate having a non-uniform thickness from medial to lateral. In still a further detailed embodiment, at least two of the plurality of guides each includes an endplate having a non-uniform thickness from anterior to posterior. In a more detailed embodiment, at least two of the plurality of guides each includes an acetabular component having a plurality of tabs at least partially defining an orifice. In a more detailed embodiment, at least two of the plurality of guides each includes an endplate at least partially defining a plurality of orifices. In another more detailed embodiment, at least two of the plurality of guide each include a femoral ball as part of the partial femoral component, each femoral ball is mounted to respective endplate, and each respective endplate is contoured to approximate the exterior of the human proximal femur. In yet another more detailed embodiment, at least two of the plurality of guide each include a femoral ball as part of the partial femoral component, each femoral ball is mounted to respective endplate, and each respective endplate is free to rotate in four directions. In still another more detailed embodiment, at least two of the plurality of guide each include a femoral ball as part of the partial femoral component, each femoral ball is mounted to respective endplate, and each respective endplate is free to rotate in less than four directions.

In yet another more detailed embodiment of the fourth aspect, at least two of the plurality of guide each include a femoral ball as part of the partial femoral component, and each femoral ball is permanently coupled to its respective acetabular cup. In still another more detailed embodiment, at least two of the plurality of guide each include a femoral ball as part of the partial femoral component, and each femoral ball is temporarily coupled to its respective acetabular cup. In a further detailed embodiment, the endplate mimics an angle of an anatomical neck of the human proximal femur. In still a further detailed embodiment, the endplates include differing tapers to determine a preferred shape of the femoral component.

It is a fifth aspect of the present invention to provide a light beam instrument comprising: (a) a light source operative to produce light; (b) at least one of a lens and a mask to utilize light from the light source to create a light image; (c) a positional controller operative to record the three dimensional position of at least one of the light beam instrument and the line of light; and, (d) a positional assembly to reposition at least one of the light beam instrument and the line of light.

In a more detailed embodiment of the fifth aspect, the light produced by the light source is a laser light. In yet another more detailed embodiment, the light produced by the light source is an infrared light. In a further detailed embodiment, the light image comprises an outline of a prosthetic trial. In still a further detailed embodiment, the light produced by the light source is a filament light. In a more detailed embodiment, the light produced by the light source is a emitting diode light.

It is a sixth aspect of the present invention to provide a light beam instrument comprising: (a) a light source operative to produce light; (b) at least one of a lens and a mask to utilize light from the light source to create a light image; (c) an image controller; and, (d) an image library communicatively coupled to the image controller.

In a more detailed embodiment of the sixth aspect, the light produced by the light source is a laser light. In yet another more detailed embodiment, the light image comprises a two dimensional image. In a further detailed embodiment, the two dimensional image comprises a hologram. In still a further detailed embodiment, the light image comprises a three dimensional image. In a more detailed embodiment, the three dimensional image comprises a hologram. In a more detailed embodiment, the light produced by the light source is an infrared light. In another more detailed embodiment, the light image comprises an outline of a prosthetic trial. In yet another more detailed embodiment, the light image comprises bone cut jig.

It is a seventh aspect of the present invention to provide a sleeve for a prosthetic insert, the sleeve comprising a support structure adapted to be secured within an intramedullary canal of a bone, the support structure including an inner surface defining an interior channel adapted to receive a prosthetic implant, the inner surface having at least one of two projections and two grooves that are adapted to align with corresponding features of the prosthetic implant to guarantee proper orientation between the support structure and prosthetic implant upon axial insertion.

In a more detailed embodiment of the seventh aspect, the inner surface includes two projections. In yet another more detailed embodiment, the two projections are at least one of linear and helical. In a further detailed embodiment, the inner surface includes two grooves. In still a further detailed embodiment, the two grooves are at least one of linear and helical. In a more detailed embodiment, the support structure includes a circular exterior surface, the support structure is circumscribed by a secondary support structure adapted to contact the wall of the bone defining the intramedullary canal, and the support structure is rotationally repositionable within the secondary support structure.

It is an eighth aspect of the present invention to provide a proximal femoral prosthetic device, the device comprising: (a) a femoral stem adapted to be seated within an intramedullary canal of a femur, and (b) an endplate mounted to the femoral stem, the endplate including a plurality of cut-outs at least partially accommodating throughput of a fastener.

In a more detailed embodiment of the eighth aspect, the fastener comprises at least one of a pin, a rod, a nail, and a screw.

It is a ninth aspect of the present invention to provide a method of projecting an image, the method comprising projecting an image onto an anatomical feature of a human, the image comprising at least one of a two dimensional image and a three dimensional image, wherein the anatomical feature comprises a bone.

In a more detailed embodiment of the ninth aspect, the image comprises at least one of a two dimensional image and a three dimensional image of a prosthetic component. In yet another more detailed embodiment, the image comprises a hologram. In a further detailed embodiment, the image comprises at least one of a two dimensional image and a three dimensional image of a cutting jig. In still a further detailed embodiment, the image is projected using a visible light source. In a more detailed embodiment, the visible light source projects laser light. In a more detailed embodiment, the image is projected using an infrared light source. In another more detailed embodiment, the infrared light source projects laser light.

It is a tenth aspect of the present invention to provide a method of aligning bones of a human, the method comprising: (a) mounting a first marker on a first bone and a second marker on a second bone while the first and second bone are aligned; (b) repositioning the first bone with respect to the second bone, where the repositioning no longer results in the first bone and the second bone being aligned; (c) displaying an image upon at least one of the first bone and the second bone; (d) repositioning the first bone with respect to the second bone using the image and the markers to align the first bone with respect to the second bone; and, (e) making a cut to at least one of the first bone and the second bone after displaying the image.

It is an eleventh aspect of the present invention to provide a method of gathering data on bones of a human, the method comprising: (a) taking a plurality of digital photographs of an exposed portion of a human bone; (b) applying a first algorithm to at least one of the plurality of digital photographs to construct a virtual outline of the exposed portion; and, (c) using the virtual outline to display a lighted outline onto the portion of the human bone using a light beam instrument.

In a more detailed embodiment of the eleventh aspect, the method also includes modifying the lighted outline to create a modified lighted outline that better approximates the anatomical outline of the human bone, recording the dimensions of the modified lighted outline, applying a second algorithm to the recorded dimensions to construct a virtual image of at least one of a trial prosthetic and a bone cutting jig, and using the virtual image to display a lighted image onto the portion of the human bone using the light beam instrument.

It is a twelfth aspect of the present invention to provide a cutting guide for use with total hip arthroplasty, the cutting guide comprising an arcuate guide for coupling to a proximal femur, the cutting guide including a concave section that mimics the arc of a natural femoral ball of a hip joint, the cutting guide including a retainer to fasten the cutting guide to the proximal femur.

In a more detailed embodiment of the twelfth aspect, the retainer comprises a plate adapted to be adjacent an exterior of the proximal femur, the plate including at least one through orifice to receive a fastener. In yet another more detailed embodiment, the fastener includes at least one of a pin, a screw, a dowel, and a nail. In a further detailed embodiment, the retainer comprises at least two plates adapted to be adjacent an exterior of the proximal femur, at least one of the plates including at least one through orifice to receive a fastener.

It is a thirteenth aspect of the present invention to provide a measurement instrument to measure at least one of diameter and circumference of removed femoral head.

It is a fourteenth aspect of the present invention to provide a distraction measuring device to determine a distraction force during leg manipulation of at least one of an acetabular cup, an acetabular insert, and a femoral head.

DETAILED DESCRIPTION

The exemplary embodiments of the present disclosure are described and illustrated below to encompass devices and methods of correctly implanting prosthetic components during hip replacement or revision surgery. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure.

Figure 1:
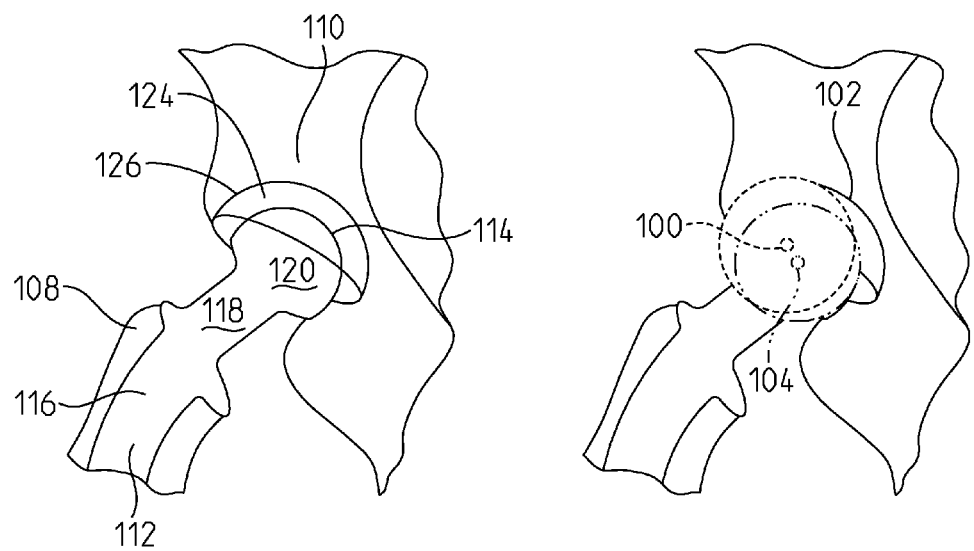
FIG. 1 is a pair of X-ray images showing the implantation of a femoral and acetabular component within a human hip joint, in addition to showing the center of the natural hip joint being offset from the center of the prosthetic joint.
Figure 2:
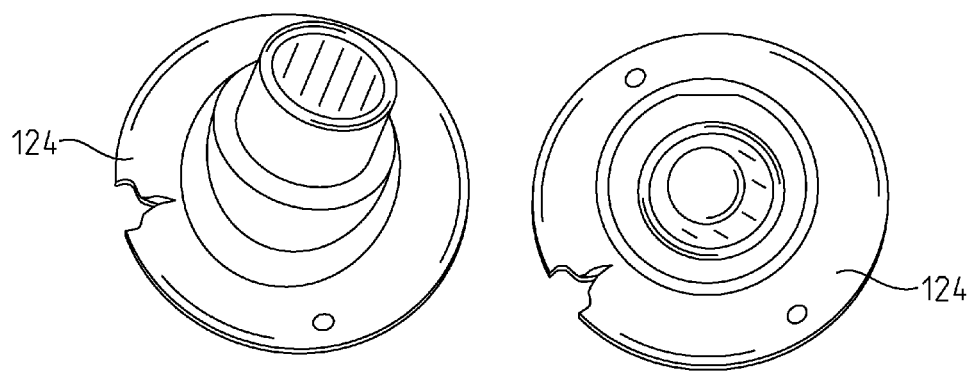
FIG. 2 is an elevated perspective view of a pair of acetabular cup inserts showing wear in the superior-lateral aspect.

Referencing FIGS. 1 and 2, an anatomical center 100 of a patient's hip joint 102 is superolateral of an implanted spherical center 104. In this depiction, a human patient has had a total hip arthroplasty (THA) procedure performed in order to replace the bearing surfaces of the patient's hip joint 102. In order to replace these bearings surfaces, THA involves the removal of a portion of the patient's femur 108, including the femoral ball and a portion of the femoral neck, as well revision of the acetabulum 110. The femoral bone removal and acetabulum reaming accommodates a femoral implant 112 and an acetabular implant 114. Most commonly, the femoral implant 112 will include a femoral stem 116 that is received within the intramedullary canal of the patient's femur, as well as a femoral neck 118 interposing a femoral ball 120. The femoral ball 120 is received within an acetabular cup insert 124 that is received within an acetabular cup 126 mounted to the patient's acetabulum 110.

Because the spherical center of the femoral implant 112 does not coincide with the anatomical center 100 of a patient's hip joint 102, the patient's soft tissue surrounding the femoral ball 120 will attempt, throughout the femoral ball's range of motion, to translate the femoral ball around the anatomical spherical center 100 of the hip joint 102. And this motion of the femoral ball 120 induced by the surrounding soft tissue, which does not coincide with the implanted spherical center 104, induces shear forces that were not present in the patient's natural hip joint. More specifically, these shear forces will induce a moment attempting to pivot the femoral ball 120 with respect to the acetabular cup insert 124, instead of rotating it within the acetabular cup insert that would mimic natural motion of the femur 108 with respect to the acetabulum 110.

A surgeon's inability to properly position the femoral ball 120 and the acetabular cup insert 124 to replicate the anatomical spherical center during THA is a major concern. Even a small offset of less than 1.0 mm may lead to an inducement of shear forces between the femoral ball 120 and the acetabular cup insert 124. Each time a patient takes a step or performs any motion, the implanted hip attempts to rotate around the anatomical spherical center, leading to an induced moment with respect to the anatomical sphere center, further inducing undesirable shear forces. In fact, common wear patterns have been observed superolateraly in polyethylene acetabular cup inserts removed from patients during a subsequent hip surgery. It has been hypothesized by the instant inventor that soft tissue surrounding the femoral implant 112 influences the motion of the femoral ball 120, rotating around the anatomical center of the natural hip joint and that this influenced motion causes more than 95% of all hip replacements to experience separation between the femoral ball 120 and the acetabular cup insert 124. Moreover, this influenced motion of the femoral ball 120 may be the primary reason for dislocation of the femoral ball 120 from the acetabular cup insert 124.

At present, surgeons initially cut the neck 144 of the femur 108 and detach the femoral head 138 from the acetabulum 110. Then, the surgeon reams out the acetabulum 110, without guides and/or knowledge of the original orientation of the anatomical acetabulum sphere. Thereafter, the surgeon prepares the femur for insertion of the prosthetic femoral stem 116. Unfortunately, no technology is used to maintain the anatomical concentric spheres as the acetabular and femoral components are inserted into the bone (femur and pelvis) separately and then the femoral head is "popped" into place with the acetabular cup. As discussed previously, these techniques lead to induced shear forces, torques, and stress on the implant components because the patient's musculoskeletal structure retains the memory of rotating the femur with respect to the pelvis around the anatomical center of the hip joint and not the hip implant's center. In other words, the lack of coincidence between the hip implant's center and the anatomical center induces shear forces, torques, and stresses on the implant components.

Figure 3:
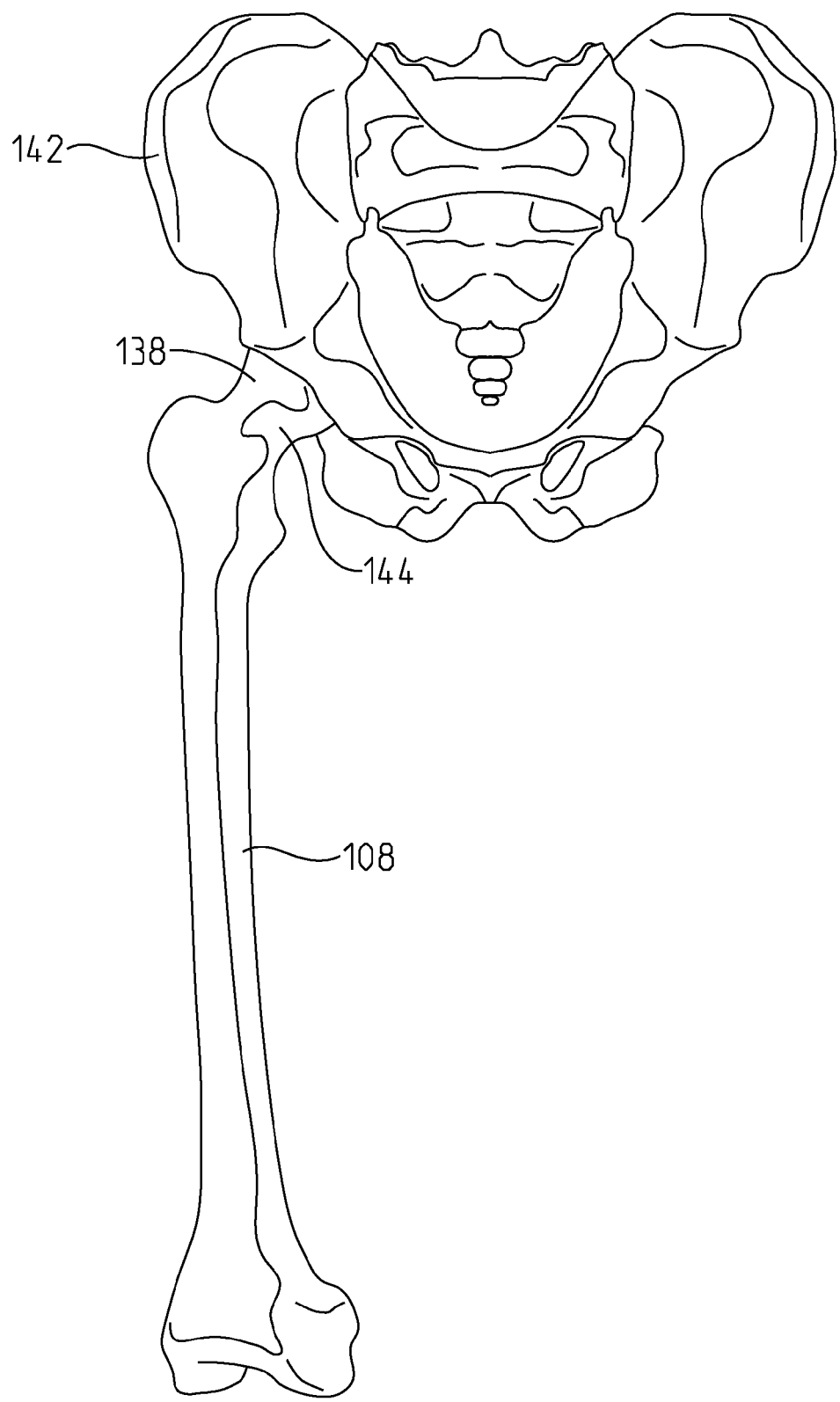
FIG. 3 is a frontal view of a human pelvis and a right femur working together to form a hip joint.
Figure 4:
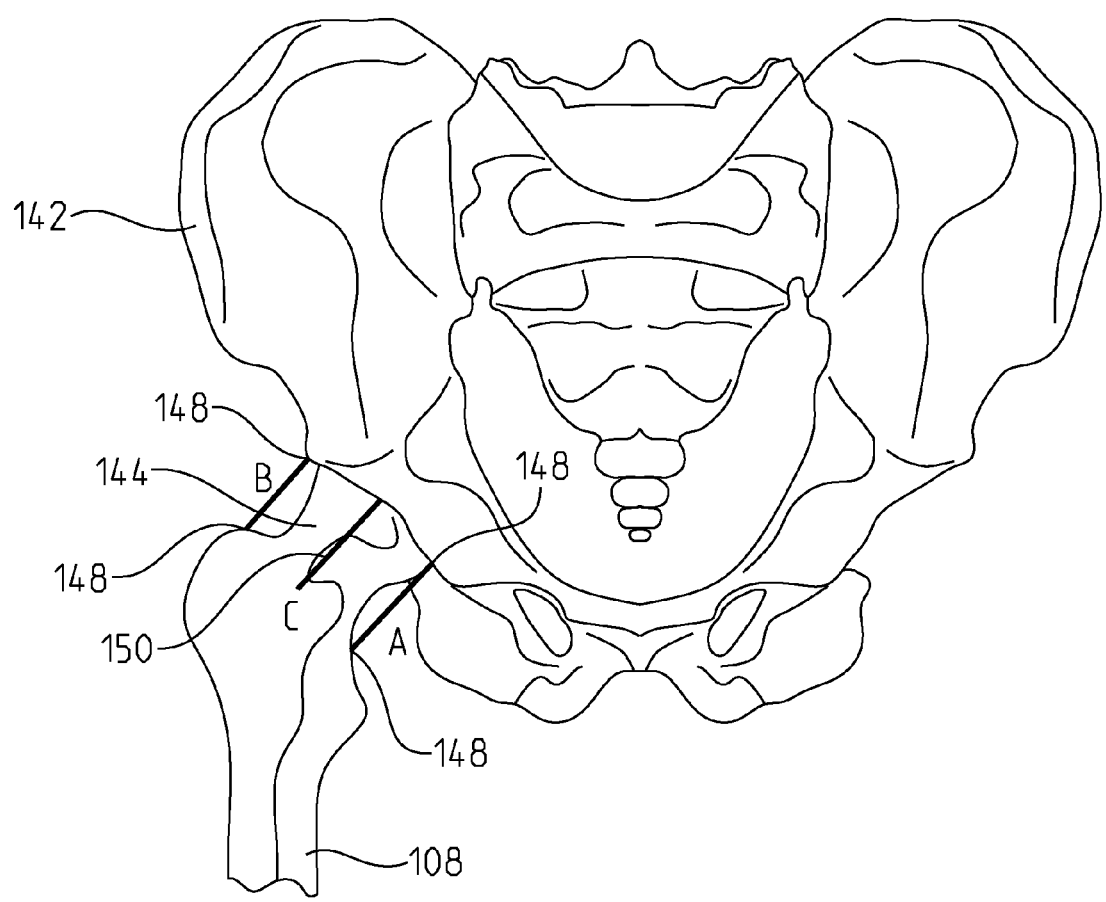
FIG. 4 is a magnified view, from the front, of a human pelvis and a right femur working together to form a hip joint marked up to show measurements and inserted pins to document boney landmarks between the pelvis and the femur and alignment of the femoral neck with respect to the pelvis.

Referring to FIGS. 3 and 4, numerous methodologies may be used to locate the anatomical spherical center of the hip joint, which can include computer assisted surgery, differing imaging modalities such MRI, CT, fluoroscopy, ultrasound, x-rays, and utilization of bone pin markers or other marker techniques, as well as utilization of an intra-operative jig or guide. Some concerns associated with certain of these techniques include, without limitation: (1) the imaging techniques and computer assisted surgery are pre-operative and require the surgeon to do pre-operative planning; (2) the techniques induce added time and complexity to the surgery; (3) the techniques add significant expense to the surgery; and (4) the techniques have an inherent error that would not permit the surgeon to accurately find the anatomical center of the hip joint.

As will be described in greater detail hereafter, a novel technique and associated instruments for finding and maintaining the anatomical center of the hip joint includes utilization of a novel trial component allowing a surgeon to more easily find the anatomical center of the hip joint and to position the implanted components to mimic the anatomical center of the hip joint. This exemplary technique does not add significant additional time or money to the THA procedure, does not require pre-operative planning using an imaging modality, and does not require the surgeon to learn how to use a software package associated with a computer assisted surgical technique.

Initially, before the surgeon makes any bone cuts, he will assess the orientation and shape of the patient's natural femoral head 138 with respect to the pelvis 142 and locate the spherical center of the hip joint, as shown in FIG. 3. As discussed previously, the spherical center of the hip joint may be located using many different techniques. But locating the spherical center of the hip joint as described herein will preferably be done without introducing significant extra cost, excessive time, and increased complexity to the surgery.

As shown in FIG. 4, the surgeon keeps track of the relative orientation and position of the femur 108 with respect to the pelvis 142, which includes keeping track of the angle of the femoral neck 144 with respect to landmarks defined on the pelvis and noting distances between the femur and the pelvis at various points that are introduced by the surgeon, but not necessarily specific. Before any bone cuts are made, the surgeon marks at least four points 148 (two on the femur 108 and two on the pelvis 142) on the two bones comprising the hip joint and records two distance measurements between corresponding sets of points, identified in FIG. 4 as distance A and distance B. However, it will be understood that more than four points 148 may be used to establish more than two distance measurements between the pelvis and femur. The points 148 may comprise physical or virtual pins or markers inserted into or otherwise mounted to the respective bone. In addition to the distance measurements, one or more pins or markers 150 may be mounted to the femur 108 and/or pelvis 142 to record anatomical angles, such as anteversion of the femoral ball and femoral neck with respect to the acetabulum. After the distance measurements and angular measurements have been taken, any pins or markers previously mounted to the femur and pelvis may be removed. But it is preferred that any mounting location be preserved for later attachment of the pin or marker.

It is also within the scope of the invention to utilize pins and associated sleeves, whereas the sleeves are inserted into the bone and the pin is then inserted into the sleeve. In such a circumstance, each pin may be removed but its associated sleeve, having a slightly larger or smaller radius than the pin or marker, will be maintained within the respective bone. This retained sleeve within the bone allows each pin to be replaced at any time.

An alternative method that may be used for aligning femoral neck angles and is through the use of lasers and/or light beams or even three-dimensional holographic images. Essentially, a surgeon has a laser or some other light beam instrument above the operating room table. The use of light beams provides a relatively easy, less expensive, and much less complicated alternative to computer assisted orthopaedic surgery.

Figure 5:
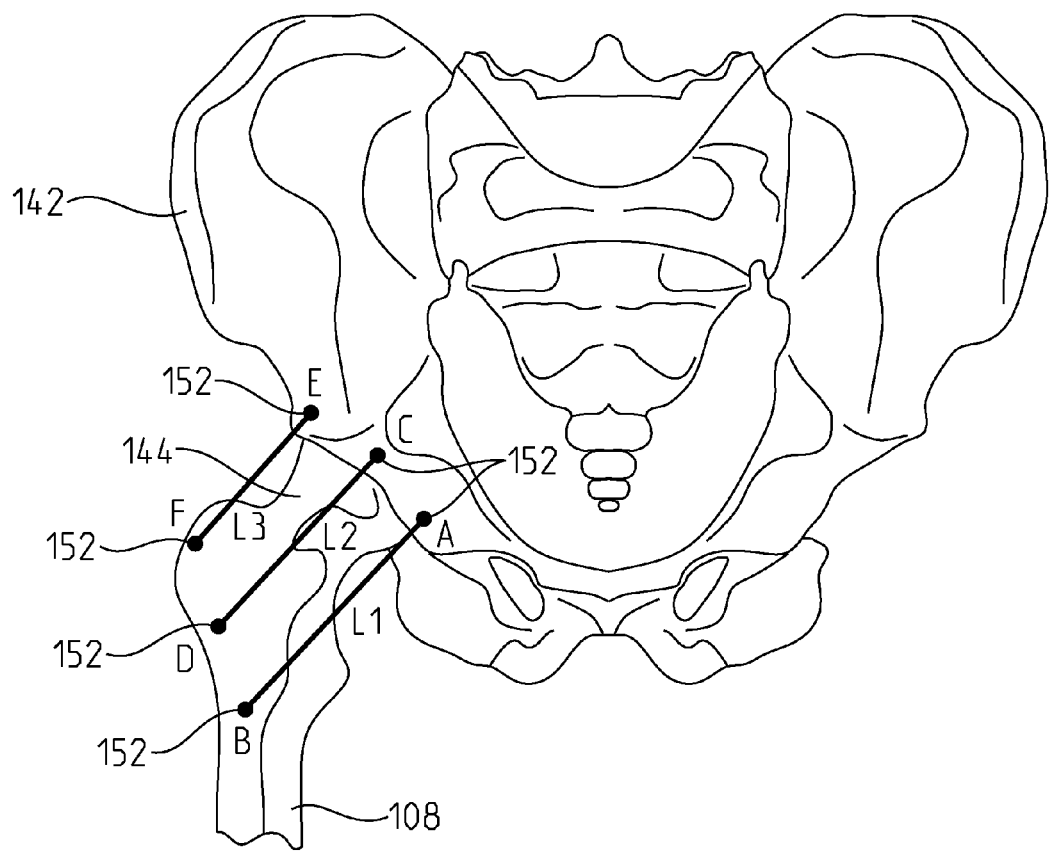
FIG. 5 is a magnified view, from the front, of a human pelvis and a right femur working together to form a hip joint with a plurality of inserted pins on the femur and on the pelvis that could be used to define specific lines and distances between those pins.
Figure 18:
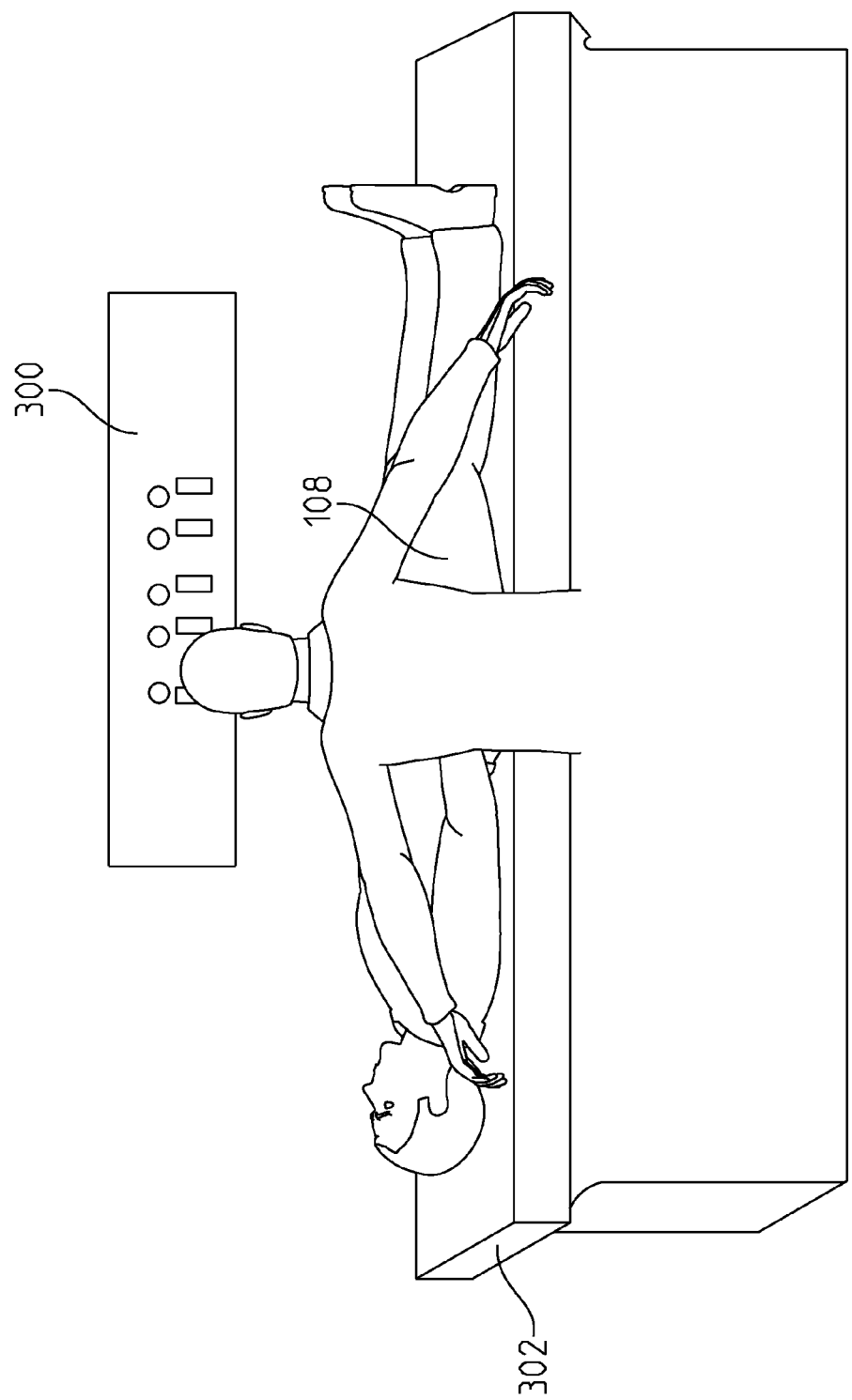
FIG. 18 is an elevated perspective view of an exemplary operating room showing the position of an operating table, a patient positioned supine, and a light beam instrument positioned over the operating table.

Referring to FIGS. 5 and 18, an even further alternative method makes use of a laser or other light beam instrument 300 above the operating table 302 to record the orientation and position of the femur 108 and the pelvis 142 (specifically, the acetabulum 110) prior to joint separation and before any bone cuts are made. Although lasers are presently used in other industries like land development and carpentry and even in your home to hang a picture on the wall, the instant inventor is unaware of lasers being used during a surgical procedure to aid in bone cuts and implantation of prosthetic components. These lasers, for other industries, could be purchased off the shelf, but for the medical application discussed in this patent, a specialized instrument is disclosed.

In essence, a laser is a device that emits light (electromagnetic radiation) through a process of optical amplification based on the stimulated emission of photons. The term "laser" originated as an acronym for *Light Amplification by Stimulated Emission of Radiation*. The emitted laser light is notable for its high degree of spatial and temporal coherence, unattainable using other technologies. Spatial coherence typically is expressed through the output being a narrow beam which is diffraction-limited, often a so-called a "pencil beam." Laser beams can be focused to very tiny spots, achieving a very high irradiance. Or laser beams can be launched into a beam of very low divergence in order to concentrate its power at a large distance. Temporal (or longitudinal) coherence implies a polarized wave at a single frequency whose phase is correlated over a relatively large distance (the coherence length) along the beam. A beam produced by a thermal or other incoherent light source has an instantaneous amplitude and phase which vary randomly with respect to time and position, and thus a very short coherence length. Most so-called "single wavelength" lasers actually produce radiation in several modes having slightly different frequencies (wavelengths), often not in a single polarization. And although temporal coherence implies monochromaticity, there are even lasers that emit a broad spectrum of light, or emit different wavelengths of light simultaneously. There are some lasers that are not single spatial mode and consequently these light beams diverge more than required by the diffraction limit. However all such devices are classified as "lasers" based on their method of producing that light: stimulated emission.

For the instant medical application(s), a laser beam or light source is focused to very small spots on the bone or very thin lines representing anatomical landmarks and/or bone or implant component angles. Although lasers are presently used for eye surgery, the application for this invention is quite different. The present invention does not use light to ablate or make any cuts in tissue. Rather, the light is utilized to create virtual jig or cutting guide.

At present, it is difficult for a surgeon to align cutting guides properly for THA. The use of lasers to create a virtual jig or cutting guide is revolutionary for hip joint surgery because it allows the surgeon to properly place instruments and to make accurate cuts without the use of physical guides and/or jigs. Therefore, the virtual jig or cutting guide is not physically in the way of the surgeon, nor requires sterilization before every surgery. In the present invention, one or more laser or light beam sources or generators is housed in a projection device 300 above the operating room table 302 (see FIG. 18). The main use of lasers in other industries is to project a laser "beam". For purposes of the instant application, what is projected is a laser "line" or laser "shape". The projection device 300 also includes a shutter or a variable opening so that a line of light may be created having a variable distance, on the order of 1.0 mm to 50 cm, and be projected onto the anatomical or implanted structure. In fact, this line may be used to define anatomical axes, such as the mechanical axes, which might require this projected laser line to be 2.0 meters in length. Exemplary lines of light are shown in FIG. 5. The thickness and distance of these light lines may be modified using the shutter or variable opening. In this manner, the surgeon is able to control the thickness of these lines using controls communicatively coupled to the projection device 300. It is also within the scope of the invention that the controls incorporate a voice recognition module in order to allow the surgeon to change the line thickness, distance, and/or orientation by verbal commands. Moreover, the projection device 300 is not limited to projecting lines of light. Rather, the projection device 300 is also operative to project shapes (2D and 3D) including, without limitation, images replicating physical jigs and cutting guides.

For example, a surgeon uses a light beam instrument 300 to orient a beam of light in a line ("light line") to appear on the femoral neck 144. The light beam instrument 300 allows the surgeon to rotate and translate this light line until the line appears, for example, in the middle of the femoral neck 144 or other locations with respect to the femoral neck that mimic the proper rotation of the femoral neck with respect to the pelvis 142. After the surgeon is satisfied with the position and orientation of the light line, the surgeon mounts two pins 152 (also marked as "C" and "D") onto the pelvis 142 and the femur 108, passing through the light line, to allow the proper neck angle rotation to be defined at anytime. Likewise, the surgeon could record the distance between the corresponding pins, but this is not necessary when only assessing the orientation of the neck angle. In addition, the surgeon may utilize the light beam instrument 300 to position additional pins 152 (marked, "A", "B", "E", "F") if needed by the surgeon. Accordingly, at anytime during the THA procedure, even if the femur 108 has been re-oriented many times with respect to the pelvis 142, the surgeon is able to re-orient the femur 108 with respect to the pelvis 142 and recreate any of the lines (marked, "L1", "L2", "L3") by turning on the light beam instrument 300 and aligning the pins 152 with respect to the light line.

Although the instant application describes the use of a light beam instrument with respect to total hip arthroplasty surgery, it should be noted that the light beam instrument may be used directly in surgical joint replacement or revision procedures, in addition to any form of procedure beyond joint replacement or revision.

Figure 6:
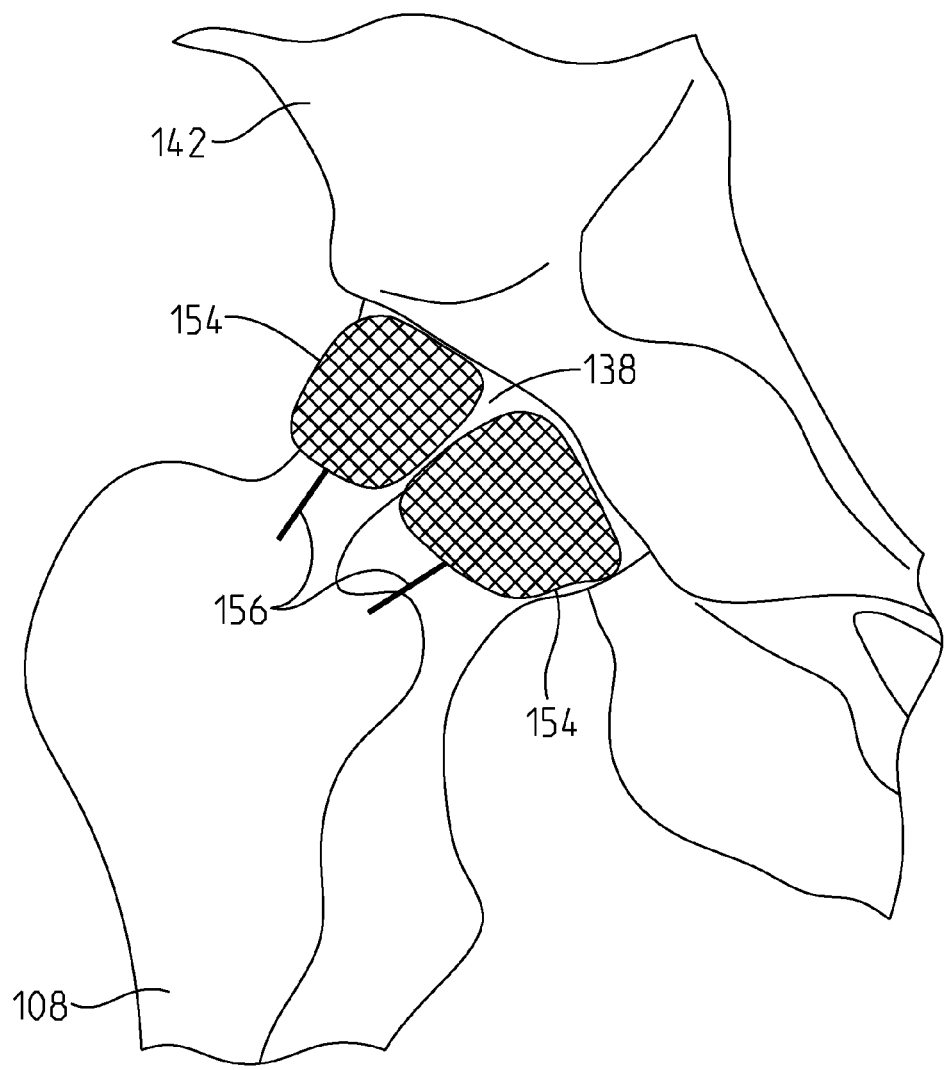
FIG. 6 is a magnified view, from the front, of a human pelvis and a right femur, where the femoral head is covered with a plurality of deformable plates that may have spherical curvature.

As shown in FIG. 6, after the orientation of the femur with respect to the pelvis has been recorded, the shape of the femoral head 138 is recorded in order to locate the anatomical spherical center of the hip joint. Recordation of the shape of the femoral head 138 can be accomplished in numerous ways. It should be understood that the following discussion includes but a subset of these numerous ways and therefore does not limit the invention disclosed herein to only these ways. A first exemplary method of recording the shape of the femoral head 138 is to use a series deformable plates 154 (four plates, for example) that are curved and/or spherical and repositionable along pins/rods 156 in order to wrap the deformable plates around the femoral head by compressing the plates against the femoral head using dials on a trial instrument that remains in contact with all of the plates and allows the surgeon to translate and orient the plates specifically on the surface of the femoral head. In this example, four plates are used, each representing one quadrant of the surface area of the femoral head. These plates may be disposable or re-usable and one or more of these plates may be securely fastened to a guided instrument (not shown). This guided instrument may have dials and levers that allow each plate to be translated to/from the bone surface and re-oriented on the bone surface. Therefore, the surgeon can translate and/or orient the plates towards the end of the femoral head and away from the pins/rods. Once the plates 154 are compressed against the femoral head 138, the orientation, size and angularity of the femoral head can be recorded. Depending on which femoral implant ball size a surgeon chooses, alternative plates 154 having a predefined curvature could be fixated to the pins/rods 156 and dialed in either separately or simultaneously to record the appropriate orientation, size and angularity of the femoral head. Although each of the plates 156 may be independently repositionable, it is also within the scope of the invention to have the plates repositioned in unison or systematically repositioned until the plates come in contact with the femoral head 138. By defining the outer geometry of the femoral head 138, the exact location of the spherical center of the hip joint can be located before the femoral head and neck 144 are removed from the femur.

Currently, trial components used in THA are not aligned with one another. Instead, the surgeon routinely places the acetabular component and the femoral component in place without aligning these components with each other. In contrast, the instant invention may make use of one or more trial components during surgery that is/are aligned according to the spherical center of the patient's natural hip joint being replaced or revised. The THA trial components may be either a single piece or multiple pieces and allow the trial femoral head to be securely placed into the acetabular trial component. This interaction between the trial femoral head and acetabular trial component allows the femoral head to freely rotate and be "popped" into place by inserting the head into the acetabular trial component. Moreover, the trial components may be generic, or have limited applicability (gender or race specific), or be patient-specific. In addition, the trial components may be reusable or may be disposable.

Figure 7:
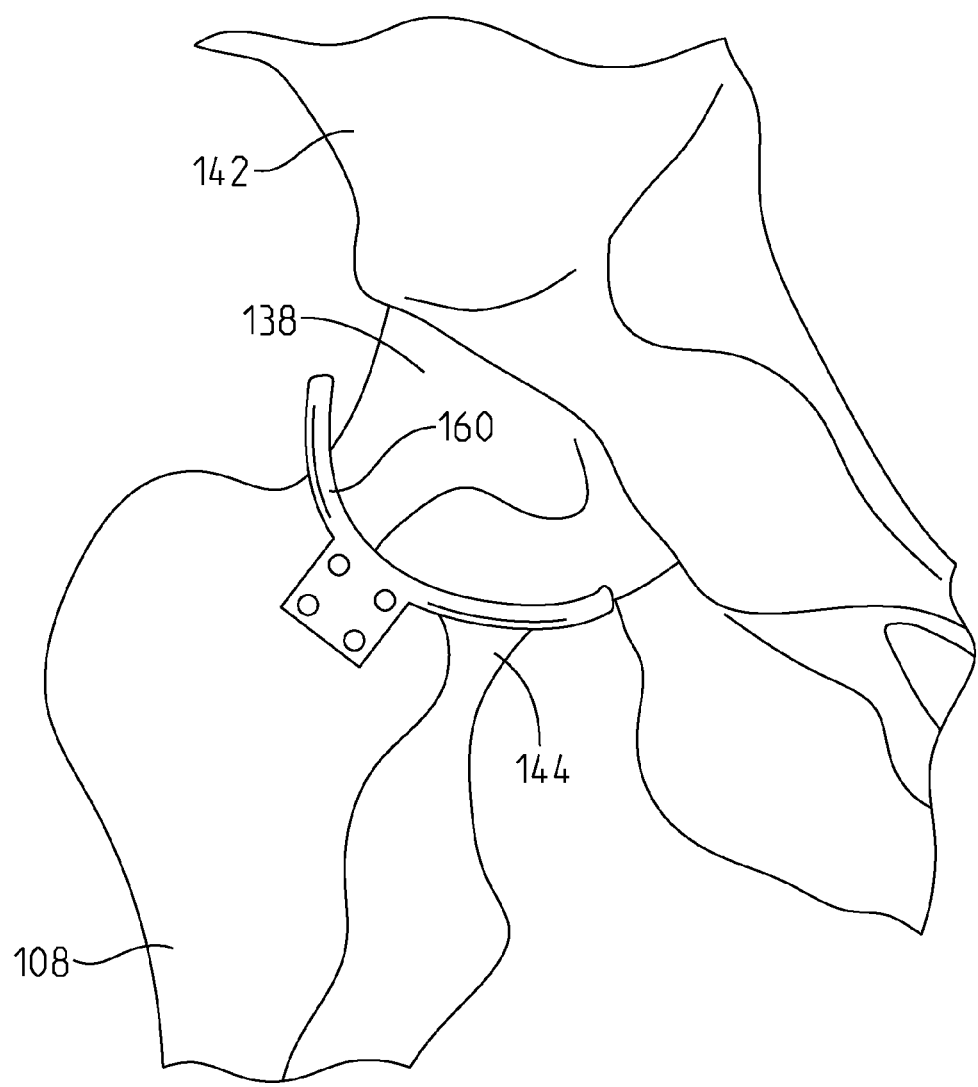
FIG. 7 is a magnified view, from the front, of a human pelvis and a right femur, where a femoral cutting guide is mounted onto the femur, creating a cut through the femoral neck that may be straight, spherical, or rounded in shape to represent the circumference of the femoral head sphere.

In contrast to the techniques and trials currently used for THA, the instant invention may make use of an anatomical sphere interposing the femoral neck and pelvis in order to replicate the size and spherical curvature of at least one of the patient's femoral head bearing surface and acetabular cup bearing surface as a means to utilize a single sphere necessarily having one central point. More specifically, the correct acetabulum sphere is one whose anatomical femoral head sphere surface maintains contact with the weight-bearing portion during gait of the anatomical acetabulum sphere. Referencing FIG. 7, in order to size the anatomical sphere, a surgeon uses a cutting guide 160 replicating the spherical shape of the patient's natural femoral head 138. For instance, in a TKA, guides are routinely used make bone cuts. In THA, guides are not routinely used. This cutting guide 160 is mounted onto the femur 108 and provides for a spherical or uniform arcuate cut of the femur that removes the natural femoral head 138 and any potentially a portion of the femoral neck 144. The guide could be mounted onto the femur 108 using a clamp, pins, as, or another method for fixating the guide to the femur. The surgeon could change the size and shape of the circumference of the cutting guide by using a dial on the handle. Once the spherical shape of the guide matches the spherical shape of the femoral head, the guide is fixated to the femur 108. Although it is recommended for this cut to spherical or rounded, representing the shape of the femoral head circumference, this cut could also be straight perpendicular to axis through the femoral head, passing through the center of femoral neck. This cut may be of any shape, but it is advantageous that this cut be spherical in its arc.

Figure 8:
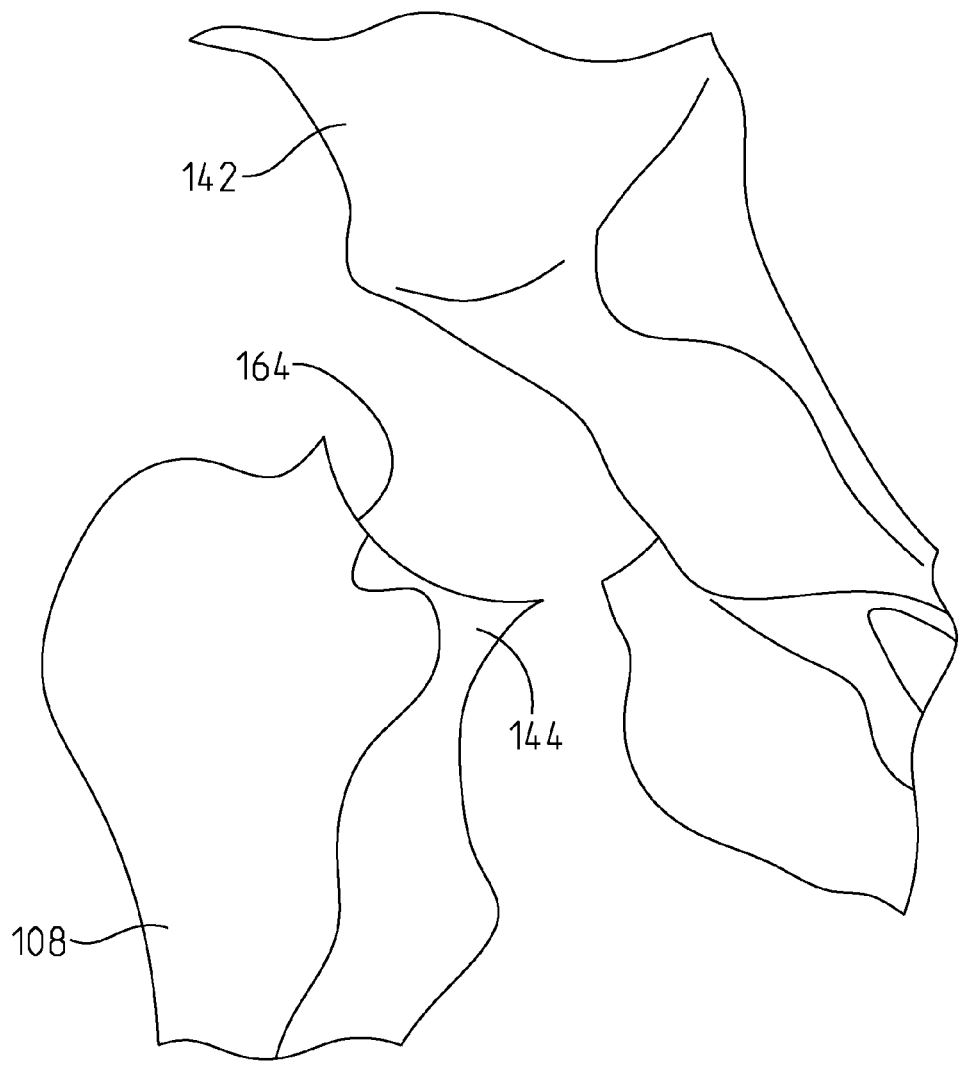
FIG. 8 is a magnified view, from the front, of a human pelvis and a right femur after a cut is made to the femur of FIG. 7 to remove the femoral head.

As shown in FIG. 8, a cut to the proximal femur 108 is made to remove the femoral head 138 and a portion of the femoral neck 144. At this time, the surgeon can visually inspect the femoral head and view its curvature. Using a measuring instrument that measures the femoral head circumference and/or diameter and/or shape, the surgeon could then choose the proper femoral head guide. The measurement of the femoral head may be made with a measurement device, a digital recording device, or an instrumented jig that is placed on the femoral head, possibly in the shape of the jig in FIG. 7, whereas a dial may be used to expand and detract the curved prongs until one or more contacts the surface area of the femoral head. After the cut, the proximal femur 108 includes an arcuate depression 164 that is sized to receive a sphere. It should be noted that the cut into the proximal femur 108 may be spherical, or the cut may have a constant arcuate profile from anterior to posterior. This constant arcuate profile has a uniform cross section from anterior to posterior, unlike the spherical cut, but is nonetheless operative to receive a prosthetic trial sphere given that the arcuate cut has the same radius as would be used for making a spherical cut into the femur.

Figure 9:
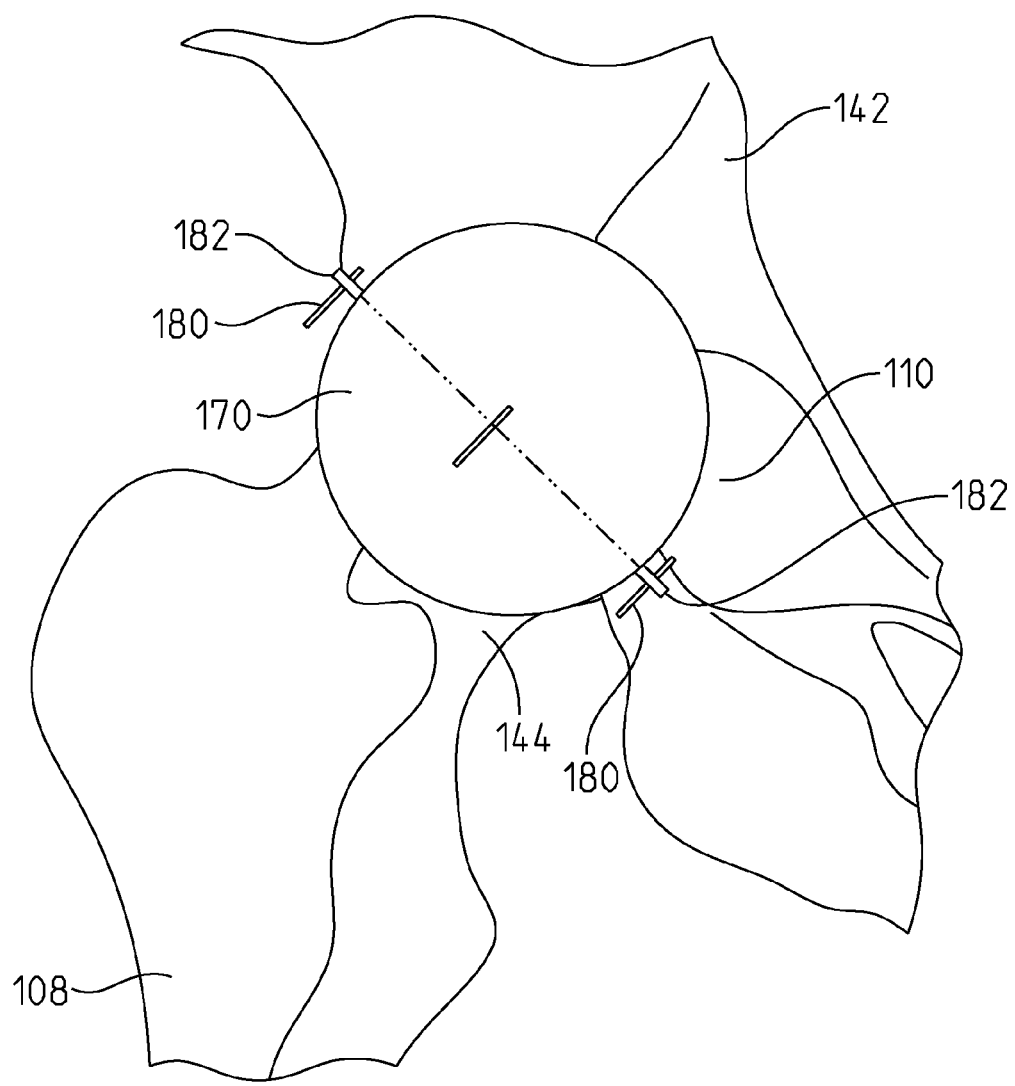
FIG. 9 is a magnified view, from the front, of the human hip joint area of FIG. 8 after a positional guide is positioned in between the femur and pelvis.
Figure 10:
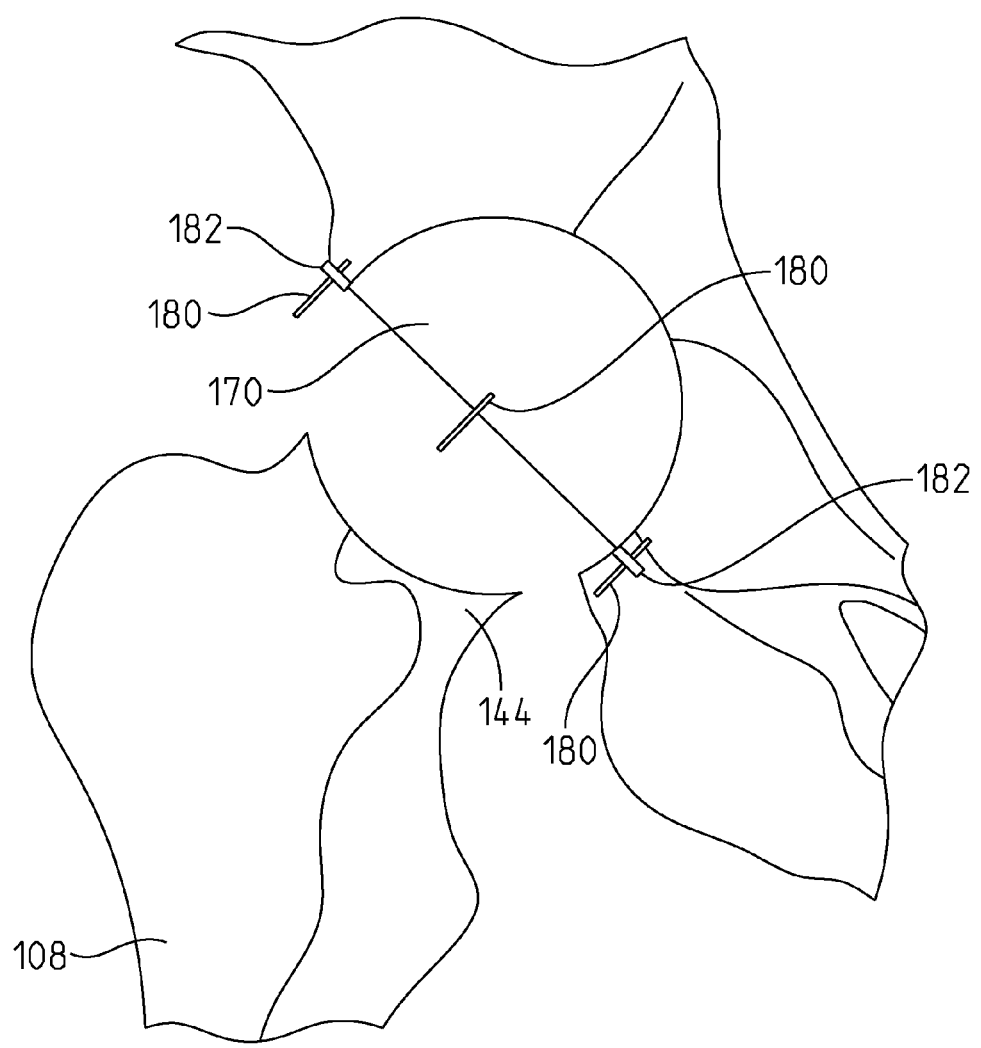
FIG. 10 is a magnified view, from the front, of the human hip joint area of FIG. 9 after half of the positional guide has been removed.
Figure 11:
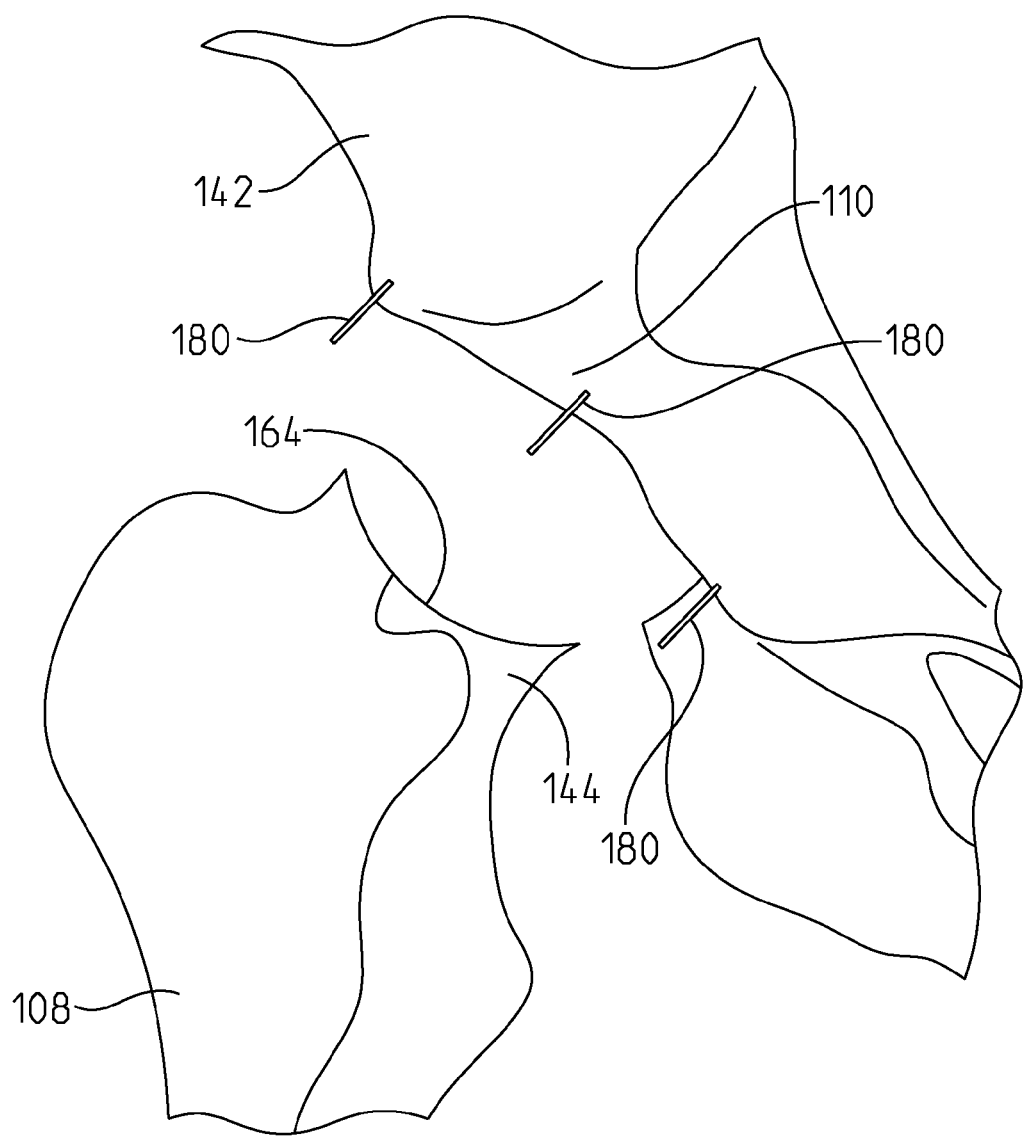
FIG. 11 is a magnified view, from the front, of the human hip joint area of FIG. 10 after the positional guide has been removed.

Referring to FIGS. 9-11, a positional guide 170 having a spherical shape is inserted into the acetabulum 110 and positioned in contact with the femoral neck 144. In this exemplary embodiment, the spherical shape is comprised of two semispherical sections mounted to one another and removable from one another. Once the guide 170 is positioned properly by fitting the inner portion of the spherical guide into the acetabulum and the outer portion next to the femoral neck, a series of holes are drilled through a series of tabs 182 (using the tabs as an axial guide for the holes) that extend radially outward from the exterior of the proximal semispherical section and into the acetabulum 110. The surgeon can re-orient the guide until the position and orientation matches with the position and orientation of the femoral head that was removed. This guide could be a perfect sphere in shape, or the inner portion of the guide could be of a shape that is anatomical with respect to the acetabulum or the inner portion of the sphere could be just a rim inserts only a small amount into the acetabulum. In fact the inner portion of this sphere may take on any shape, as long as it is inserted into the acetabulum, but it may be advantageous for this shape to be spherical or anatomical. Although it is recommend that the outer portion of the guide be spherical to mate with a spherical cut in the proximal femur, it should be understood that the outer portion may be of any shape. For example, the outer portion may have a box-like shape where the outer edge may be in contact with a straight cut on the femur. If a box-like shape is used, it is preferable for the surgeon or another to measure the diameter along the three principal axes, to ensure that the box is shaped to mimic the circumference and diameters of the femoral head. After the holes are drilled into the acetabulum 110, a series of pins 180 are inserted (one pin for each hole) through the tabs 182 and into the holes in the acetabulum 110, thereby locking the guide 170 in position with respect to the acetabulum. After the pins 180 are inserted through the tabs 182, the guide 170 is removed and a reamer (not shown) is used to ream the acetabulum 110 using the pins 180 as alignment guides. To use the reamer, more rigid guide pins may be used to guide the reamer, or the guide pins may be used to insert a central guide pin, thereby allowing the reamer to ream out the acetabulum along the central principal axis of the acetabulum sphere. Ideally, the inner portion of the femoral head guide is either spherical or anatomical in shape so that when the outer portion is removed, the inner portion is reminiscent of an acetabular cup so the surgeon could visible inspect the position and orientation of the femoral head guide cup, which will ultimately be the position and orientation of the implanted cup after all the final acetabulum cuts are made.

If the acetabulum is damaged, for example by arthritis, the guide 170 may be aligned, primarily off of the proximal femur and inserted into the acetabulum. Likewise, if the proximal femur is damaged, the guide 170 may be aligned more so off of the acetabulum and then inserted next to the proximal femur.

Figure 12:
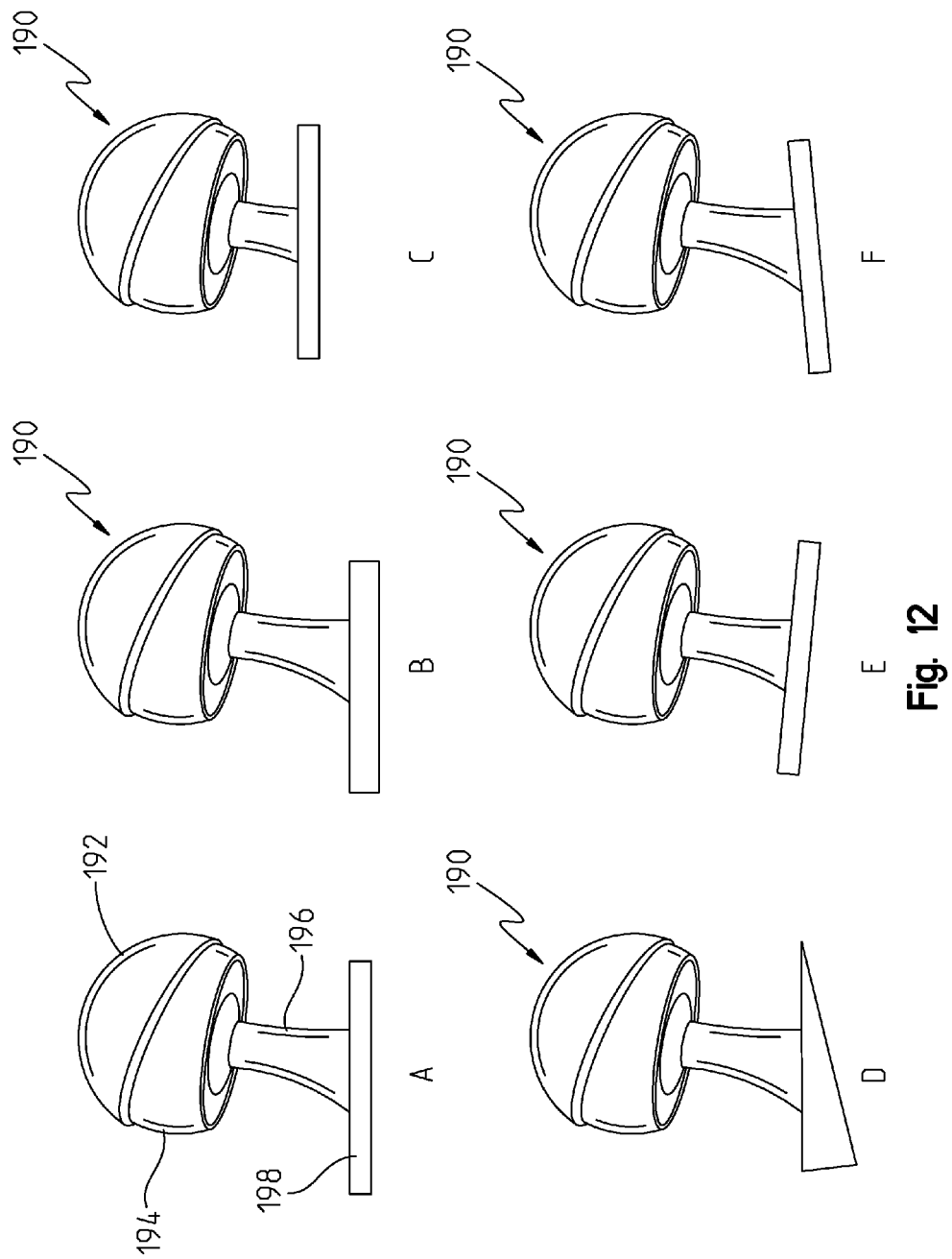
FIG. 12 comprises a series of elevated perspective view of exemplary hip joint trials.

Referencing FIG. 12, after the acetabulum 110 has been reamed, a portion of a prosthetic trial 190 is inserted within the acetabulum 110 using the pins 180 as alignment guides. The size of the spherical head in this trial 190 may be variable in size and shape depending on how much bone and/or cartilage was removed during the reaming process. Specifically, this prosthetic trial 190 includes an acetabular component 192 and a femoral ball 194 inserted therein. It is the acetabular component 192 that is temporarily inserted into and mounted to the reamed acetabulum 110. The femoral ball 194 of the trial 190 is coupled to a femoral neck 196 having an endplate 198.

As shown in FIG. 12, exemplary trials 190 may be modular so that the femoral ball 194 is repositionable with respect to the acetabular component 192 and/or the femoral neck 196 is repositionable with respect to the endplate 198. In contrast, the exemplary trials 190 may be integrated or a single piece to inhibit movement between the respective components so that the orientation and position of the femoral ball 194 with respect to the acetabular component 192 is fixed and/or the orientation and position of the femoral neck 196 with respect to the endplate 198 is fixed. Moreover, the exemplary trails 190 may embody a neutral shape position (A) or have a thicker base (B), or have variable neck lengths (C), or have an irregular base shapes (D), or have a clockwise rotated base shape (E), or have a counterclockwise rotated base shape (F).

Figure 13:
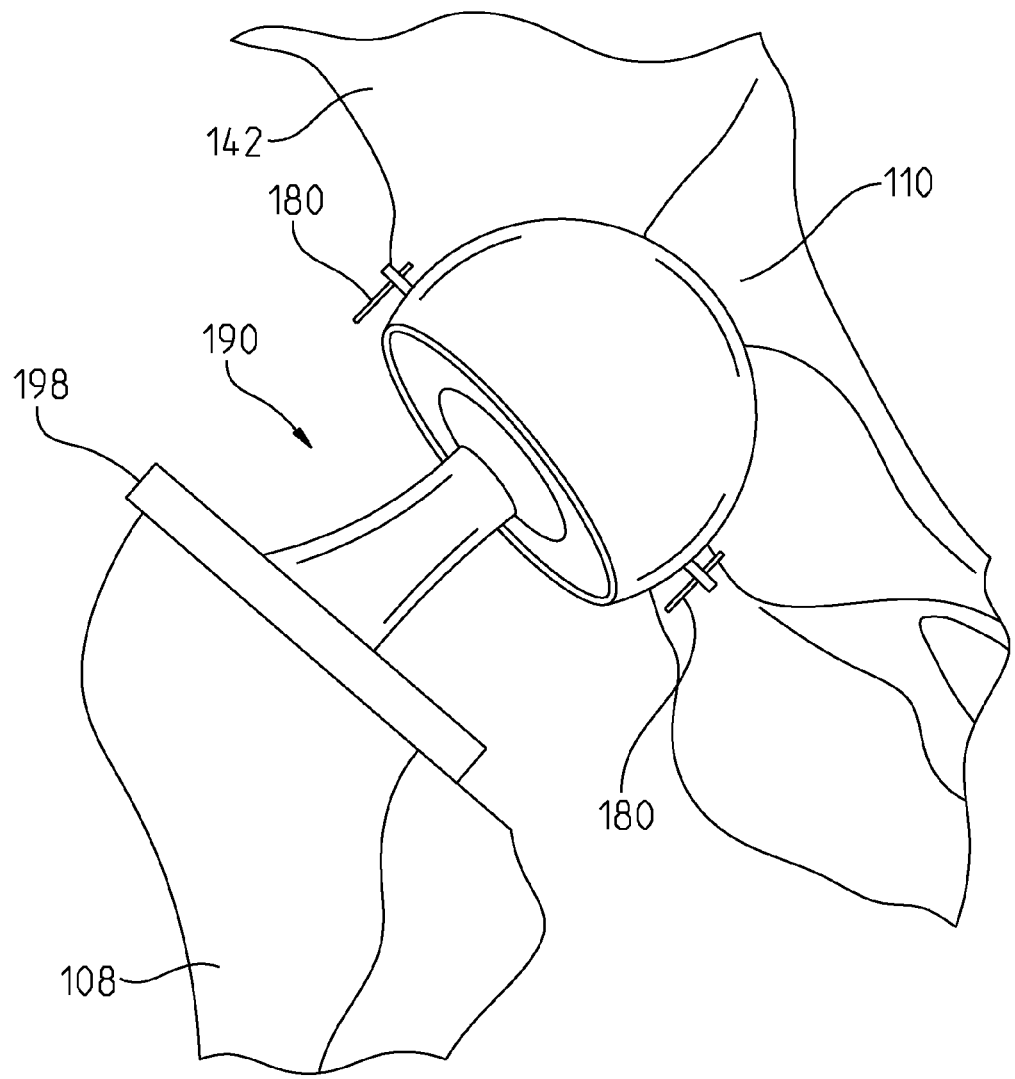
FIG. 13 is a magnified view, from the front, of the human hip joint area of FIG. 11 after installation of a hip joint trial.
Figure 14:
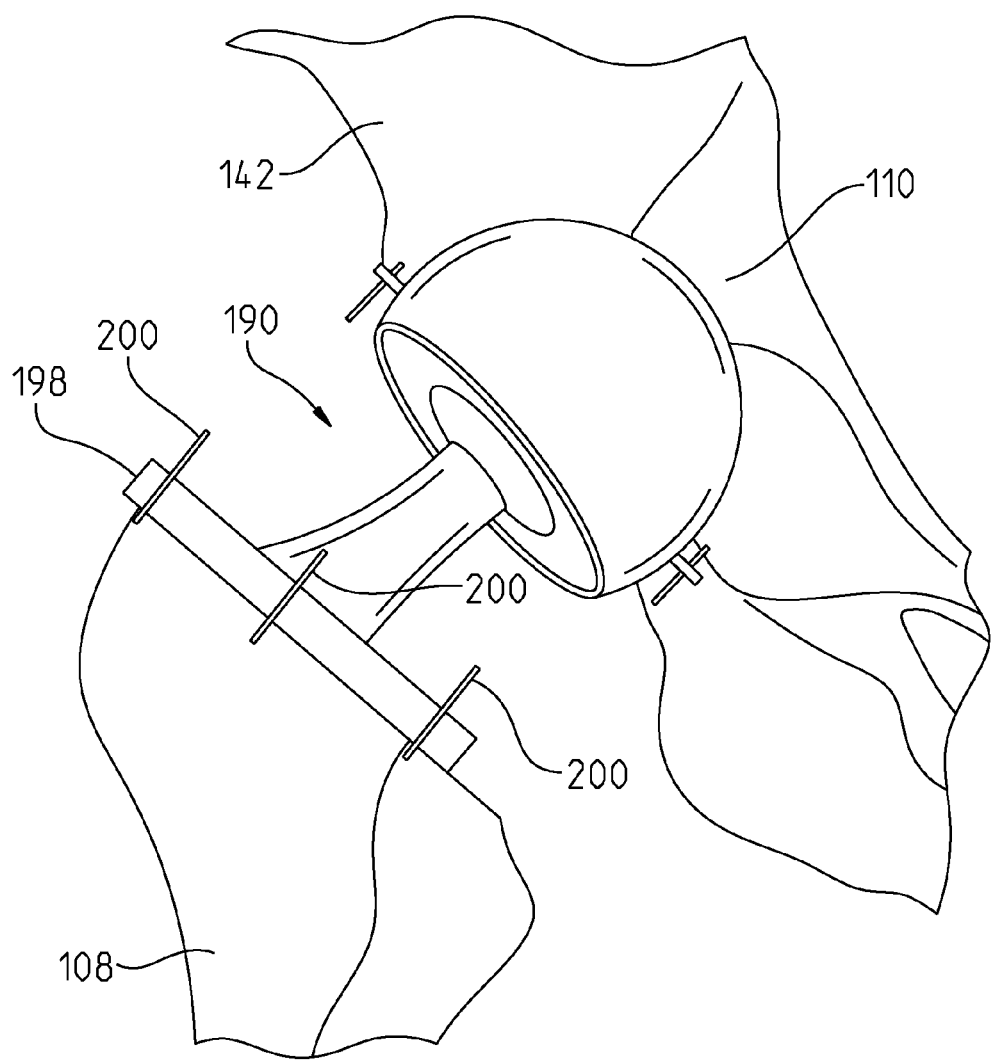
FIG. 14 is a magnified view, from the front, of the human hip joint area of FIG. 11 after installation of a hip joint trial and after installation of a plurality of guide pins in the pelvis.

Referring to FIGS. 12-14, one at a time, the various trials 190 may be temporarily mounted to the acetabulum 110 and aligned using the pins 180 to maintain proper acetabular cup orientation. At the same time, the femoral aspect of the trial 190 is used by the surgeon to properly maintain the orientation and position of the femur 108.

Figure 15:
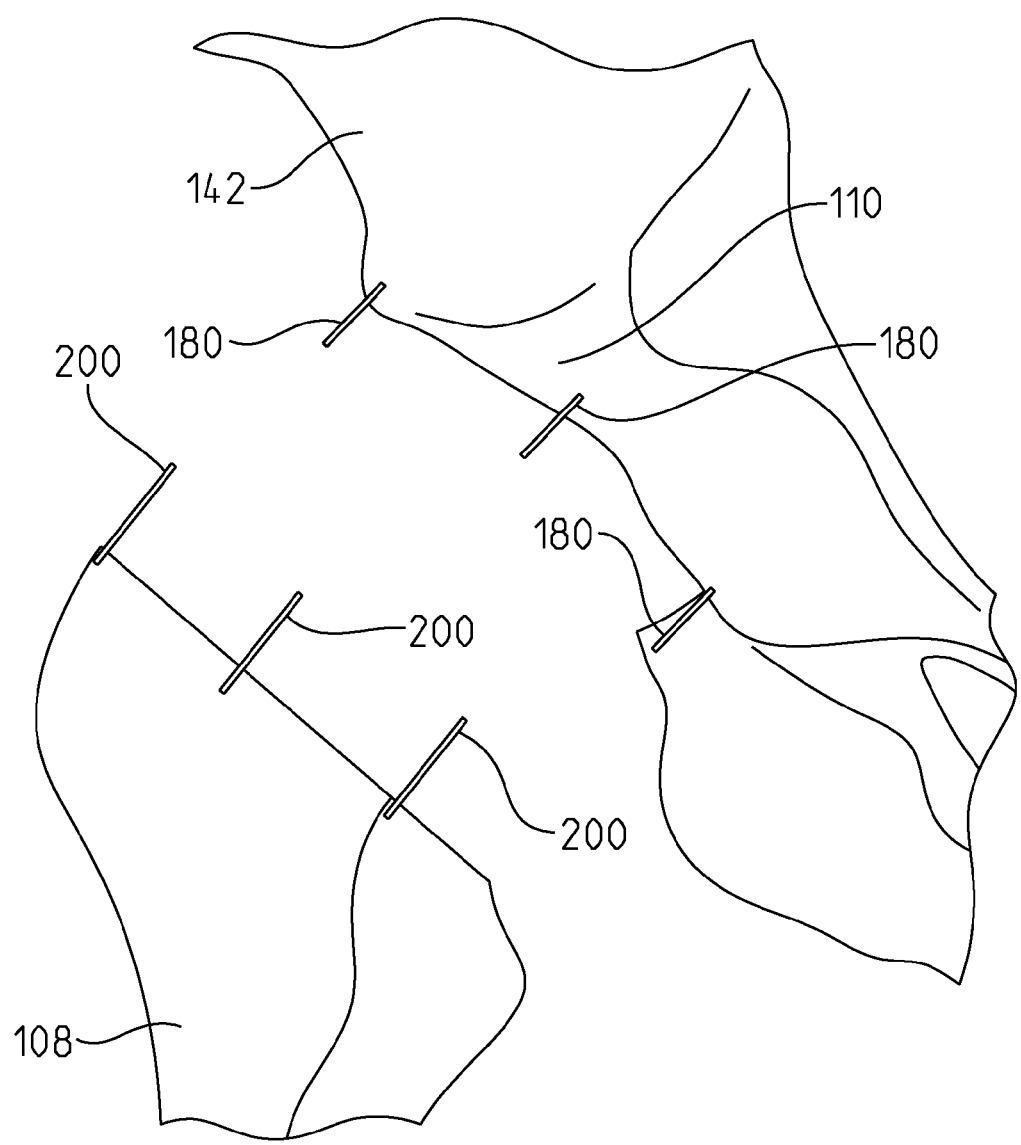
FIG. 15 is a magnified view, from the front, of the human hip joint area of FIG. 14 after removal of the hip joint trial and retention of the plurality of guide pins in the pelvis.

Referring to FIGS. 13 and 14, after the orientation and position of the femur 108 is fixed with respect to the pelvis 142 using the trial 190, guide pins 200 inserted through the femoral endplate 198, allowing for proper cuts to be made, maintaining concentric anatomical spheres. The femoral portion of this trial 190 may be free to rotate around all three axes or a locking mechanism may be used so that when the proper orientation of the femoral neck coincides with anatomical femoral neck, the angle is locked into place. While the acetabular component 192 is inserted within the reamed acetabulum 110, using the previously inserted guide pins 180, the surgeon is ready to mark the final cut of the femoral neck 144 using the trial 190. By using the trial 190, which is mounted to the pelvis 142, the resulting mark for the final cut of the proximal femur 108 accounts for the orientation and position of the trial and allows concentric spheres (anatomical acetabulum sphere and femoral sphere) to be maintained. Although it is shown in FIGS. 13 and 14 that the trial 190 rests on the proximal femur, it could also be inserted into the proximal femur and/or guided around the proximal femur. Referencing FIGS. 14 and 15, after the guide pins 200 are inserted into the femur 108, the trial 190 is removed from both the femur 108 and the pelvis 142. Thereafter, a cutting guide (not shown) is mounted onto the femur 108 using the pins 200 as a guide to ensure the alignment of the eventual femur cut.

Various tapers may also be implemented in this trial shown in FIG. 12. Therefore, when the acetabular cup portion of the trial is inserted into the acetabulum, it may be temporarily fixed into place using nails or other fixating devices. Then, the femoral portion of the trial may be fixated to the superior aspect of the femur. Next, the surgeon may manipulate the leg into multiple positions, visually inspecting and instrumentally measuring for impingement, possible dislocation and any other concerns that could be raised. The surgeon may then replace the femoral portion of the trial using a different taper to again inspect and measure how the femoral component is rotating with respect to the pelvis.

A distraction device may also be used that measures the amount of pull of the acetabular cup from the bone during manipulation of the femur. If the implants have concentric spheres, then the distractive and shear forces should be very low. If during this manipulation of the femur, the acetabular cup visually attempts to pull away from the bone or if the measurement device(s) detects irregular amounts of distractive or shear forces, a different trial may be used. This distraction measurement device may be a spring loaded mechanism or even a measurement device that measures distractive distance and converts this distance to a force, based on a mathematical model of the human hip joint that derives intra-operative forces using Newton's equations of motion. The mathematical models of the human body may be derived as an inverse model that measures the three rotations and translations of either the cup from the bone and/or the femoral head from the cup. Then, this motion is entered into the mathematical model to determine the forces in three directions and the torques around three directions.

Figure 24:
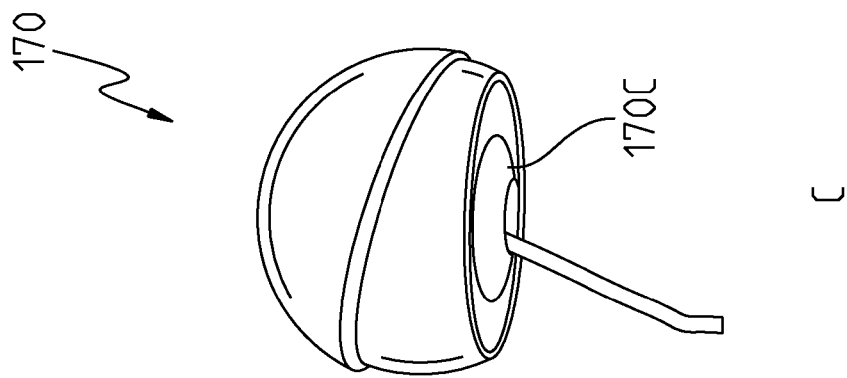
FIG. 24 comprises profile views of exemplary femoral trials in accordance with the instant invention used to determine the proper size the location of the femoral bone cut.
Figure 24:
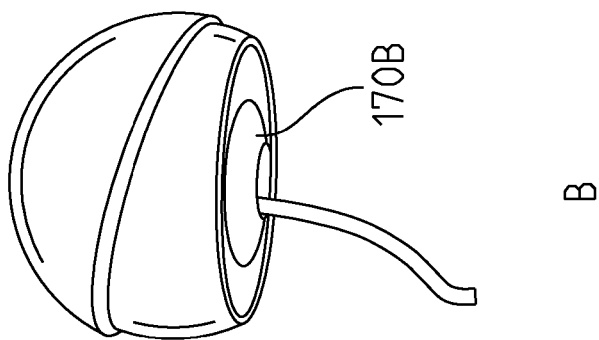
Figure 24:
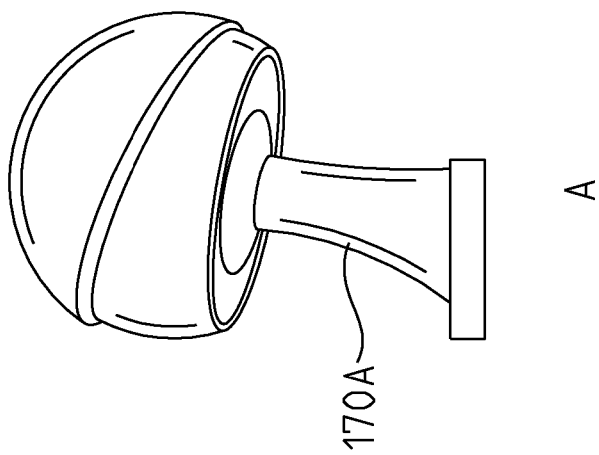

As shown in FIG. 24, an alternate method of marking the femur 108 includes using an alignment/trial instrument 170 positioned so the acetabular portion is seated within the acetabulum and the femoral portion overlies the femoral neck. The surgeon may then reposition the instrument 300 to align with the proper orientation of the intended proximal femoral cut. The alignment/trial instruments 170 may be of normal implant shape and thickness 170A, or could of proper shape and thickness for the cup and femoral ball, but much thinner for the femoral neck and proximal femoral component 170B, 170C. In particular, the femoral neck portion of the alignment/trial instruments 170B, 170C comprises a flat plate that is contoured to approximate the exterior contour of the patient's proximal femur so that the instrument may be easily placed directly on top of the proximal femur to ensure an accurate proximal femoral bone cut. The shape could also be anatomical in nature.

Figure 16:
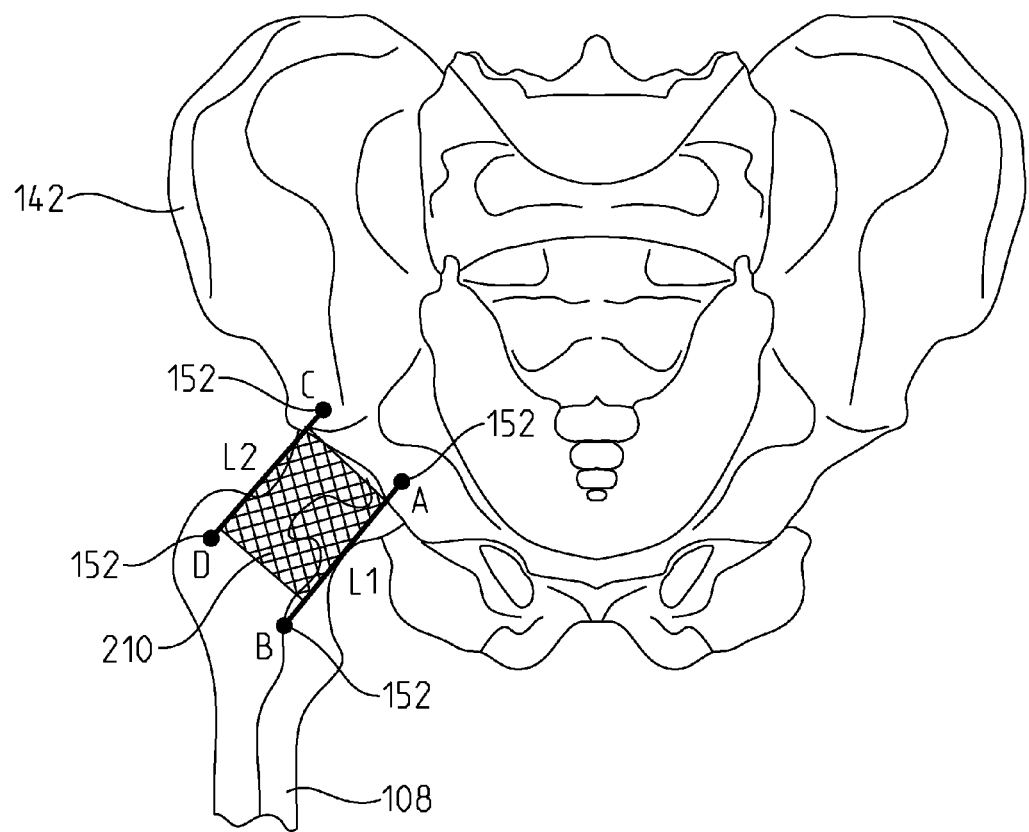
FIG. 16 is a magnified view, from the front, of the human hip joint area showing a light image superimposed onto the proximal femur.
Figure 17:
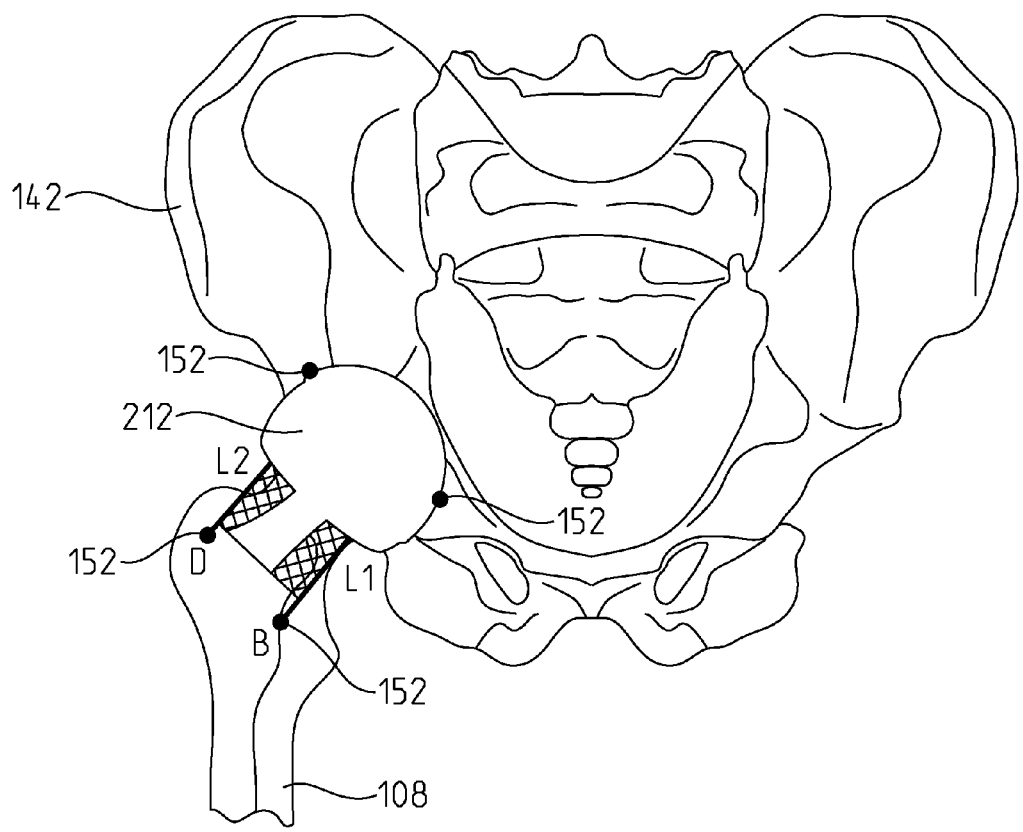
FIG. 17 is a magnified view, from the front, of the human hip joint area showing a light image superimposed onto the proximal femur.

Referring to FIGS. 16-18, a further alternative method of marking the femur 108 includes using the light beam instrument 300 previously discussed to superimpose various shapes upon the proximal femur and distal pelvis 142. Those skilled in the art will realize the virtually any two dimensional shape could be superimposed upon the proximal femur such as, without limitation, a square, a rectangle, a trapezoid, and an outline of a prosthetic hip trial. A computer algorithm may be used with this instrument 300 so that three-dimensional or planer two-dimensional anatomical bone shapes are stored within a virtual library of images. These images may be created using one or more imaging modality including, but not limited to, MRI, CT, ultrasound, and X-rays. These images may also be stored in various libraries for size, gender and ethnicity.

During surgery, the surgeon uses a handheld instrument to generate surgical data including, but not limited to, boney landmarks, orientations, and distances. This surgical data is used by a computer algorithm to initially choose which image in the various libraries best matches the data entered and then, may modify one or more images stored in the virtual library to generate an image using the instrument 300 and project this image onto the patient's anatomical bone (in this case, the proximal femur). The library images may then be superimposed onto and compared with various images in the library, may be used to create a bone from various bones, or may be morphed from one or multiple library images. Then, using controls associated with the instrument 300, the image may be fine-tuned to modify the shape, size, thickness, position, and/or orientation to best match the patient's bone. In exemplary form, the instrument 300 projects virtual jigs, implants, and/or bones onto the patient's bone representative of the ideal location for each bone cut. In addition or in the alternative, the instrument may project an image of the final implant or implant component onto the patient's bone. For example, FIG. 16 depicts a rectangular shape 210 superimposed onto the proximal femur 108 and distal pelvis 142, while FIG. 17 depicts an outline of a prosthetic hip trial 212 superimposed onto the proximal femur and distal pelvis. Moreover, at any time during the surgery, even after the surgeon has made all the bone cuts, the surgeon may turn on the light beam instrument 300 to verify the bone cuts made or to revise the bone cuts to match a particular shape, such as the outline of the intended implant. As discussed previously, even if the femur 108 has been repositioned and is out of alignment, the surgeon may utilize one or more of the pins 152 to properly orient and position the femur with respect to the pelvis 142. And after the femur 108 and pelvis 142 have been aligned, the light beam instrument 300 may be utilized to superimpose one or more shapes that represent the best or preferred implanted femoral neck shape and/or acetabular cup and/or femoral head that maintains proper biomechanics and concentric spheres of the pelvis 142 and femur 108.

This light beam instrument 300 provides a relatively easy, less expensive, and much less complicated alternative to computer assisted orthopaedic surgery. At present, many surgeons are attempting to use computer navigation to define the orientation and position of the hip joint, but this methodology can be cumbersome and difficult to learn. In the instant technique, a light beam instrument 300, controls (such as dials and/or levers) may be used to change the position and orientation of a light beam (or image) directed from the instrument above the operating room table 302 to represent angles and/or positions of the femur and/or the pelvis during surgery. A surgeon can then turn on a light beam from the instrument 300 and manually and/or audibly change the position and/or orientation of the light beam to define an anatomical feature of a bone, such as the anatomical femoral neck. Once the light beam has been positioned onto the femoral neck, defining its anatomical position and orientation, two or more pins may be inserted in the femur and/or pelvis. These pins may be used to define the anatomical bone or bone feature in question. Multiple light beams may also be used, defining as many bones or boney features as needed by the surgeon. Therefore, at anytime during the surgery, the surgeon may turn on a beam from the instrument 300 and re-orient the bones until the beam passes through the alignment pins.

Although the previous examples utilize the light beam instrument 300 to project a two-dimensional image, the projected images could also be three-dimensional using holographic images. Holographic imaging may be utilized to allow bone anatomy, bone landmarks, and implant components to be projected onto the bone using a light source. The light source, scattered from the object of reference, will be recorded and later reconstructed so that when an imaging system (a camera or an eye) views the reconstructed beam, an image of the bone and/or implant component is seen even when it is no longer present in the surgeon's field of view. The image changes as the position and orientation of the surgeon changes in exactly the same way as if the object were still present, thus making the image appear three-dimensional. This effect can be seen by the surgeon at all times, right where the orientation of the bone and/or implant component, even though each view of the image may appear to be significantly different by the surgeon, yet the three-dimensional orientation and position are correct. It should be noted that the holographic recording itself is not an image—it consists of an apparently random structure of either varying intensity, density.

Similar to the foregoing technique used to project a two-dimensional image upon the patient's bone, a computer algorithm is used in order to generate a three-dimensional image and superimpose this image onto the requisite one. Unlike the two dimensional image projection, the surgeon will be required to measure distances and orientations in all three directions. In order to create the three-dimensional image, a series of preexisting three-dimensional images are stored in a virtual library. These images will contain proper bone landmarks and distances that define orientation and position with the human body structure. These images may be rigid or deformable bodies. During surgery, the handheld device is used to define anatomical distances, positions, and orientations on the bone of the patient in question and then, the computer algorithm chooses the best initial three-dimensional bone fit and projects this three dimensional image onto the anatomical bone. Unlike using a two-dimensional image, distances from the light beam source of the light beam source instrument to the anatomical bone must be known to properly project the three-dimensional image. Without defining this distance, at multiple locations on the anatomical bone, the three-dimensional image may not be properly projected. Therefore, three-dimensional information along all three directions must be measured and entered into the computer algorithm.

An exemplary method of measuring and entering the data for processing by the computer algorithm includes using a digital camera or other recording source to take multiple photos or images of the honey anatomy, such as the femoral neck and head after the surgeon opens up the joint space. These image views may be proximal, distal, anterior, posterior, medial, and/or lateral. These images, in real-time may be sent to the light beam instrument 300 and using the instant computer algorithm, a three-dimension image, either holographic or non holographic is constructed using the three-dimensional library of bone images. Then, the best fit bone image is projected onto the patient's bone. Using dials, levers or other controls, the three-dimensional image can be re-oriented, re-sized and/or re-positioned onto the anatomical bone. Once the surgeon deems the three-dimensional image to be an accurate representation of the anatomical bone, another algorithm is used to define honey landmarks and bone cuts that are ideal for that particular patient.

Creating the three-dimensional holographic images makes use of devices that produce so-called diffraction fringes, fine patterns of light and dark that can bend the light passing through them in predictable ways. A dense enough array of fringe patterns, each bending light in a different direction, can simulate the effect of light bouncing off of a three-dimensional object. In exemplary form, one exemplary commercially available technology uses a cylinder approximately one meter high by one-half meter in diameter. Inside the cylinder, a helix spins at high speed. A two-dimensional image is projected onto the helix and then the image is projected onto the bone. It is presumed, for purposes of this example, that the images are simple CAD-like drawings. These simple images are constructed from multiple digital camera images as discussed previously. An alternative method and technology that may be used incorporates a pair of lasers that emit beams that intersect one another inside of a cube of special material. The material inside the cube glows at the intersection point. Another method uses two lasers that intersect inside a cube of a special material. The material glows at the intersection, creating an image that may then be projected onto the bone.

Initially, the surgeon points the laser of the light beam instrument 300 at a beam splitter, thereby causing the beam to be divided into two beams. Mirrors within the light beam instrument 300 are constructed along the path of the splitter so that the laser hits the bone in question. The light beam instrument 300 also includes diverging lenses in front of the mirrors so that the two beams passing through them become wide swathes of light rather than regular beams. One of the lights (object beam) will reflect off the bone in question and onto the holographic plate of the light beam instrument 300. The other light (reference beam) will hit the holographic plate only. Then, the surgeon projects the three-dimensional holographic image on the bone in question at anytime during surgery.

At present, surgeons routinely have four to ten trays of instruments and jigs for use during the surgery. Before every surgery, these instruments and jigs need to be prepared and sterilized. The foregoing light beam instrument may be used to project these instruments and jigs onto the bone, as needed by the surgeon. Each instrument is scanned using a laser scanner or is converted into three-dimensional solid objects using three-dimensional computer models. Once each instrument and various sizes are entered into the virtual library of images, the images may be re-oriented and displayed at anytime using a computer algorithm that instructs the light beam instrument to rotate and translate with respect to either a fixed or relative reference frame. The Newtonian reference frame is defined within the computer algorithm and relative reference frames are defined for each instrument. Each rotational and translational direction is defined as a function in an inverse direction model or as a generalized speed in a forward solution model. A change in direction or rotation of the displayed image may be made by the surgeon audibly, through the use of dials and/or levers (i.e., controls) or using a touch screen monitor. In fact, numerical changes to the translation matrix may also be input to define motion changes. Using for example, a touch screen instrument, the surgeon is able to touch a picture of a virtual instrument or guide and the computer algorithm instructs the light beam instrument to project it. Then a secondary library appears on the screen, whereas a surgeon can choose the correct size of the image. Then, by audible commands or using dials and levers or using his finger on the screen, the image, whether two-dimensional or three-dimensional can be repositioned. Therefore, the relative transformation matrix between the instrument and the Newtonian reference frame could be altered depending on where the instrument is in space with respect to the origin within the Newtonian reference frame. Once the surgeon has the instrument or jig in place, a stop is instituted and the relative reference frame of the instrument with respect to the Newtonian reference frame is recorded and stored for future use of the instrument. Therefore, within the computer algorithm the generalized coordinated and generalized positions, defined from the generalized speeds are changed and redefined based on global coordinate changes. This procedure may be conducted for each instrument, jig and bone, whether in two-dimensions or three-dimensions. These instruments, jigs and bones may have points, axes and cutting guides defined and positioned properly for surgical use.

As stated previously, this process may be used for three-dimensional images, holographic or non-holographic. As stated previously, holography is a technique that allows the light scattered from an object to be recorded and later reconstructed so that it appears as if the object is in the same position relative to the recording medium as it was when recorded. The image changes as the position and orientation of the viewing system changes in exactly the same way as if the object was still present, thus making the recorded image (hologram) appear three dimensional. Holograms can also be made using other types of waves.

Three-dimensional space is a geometric model of the physical universe in which we live. The three dimensions are commonly called length, width, and depth (or height), although any three mutually perpendicular directions can serve as the three dimensions.

In mathematics, Cartesian geometry describes every point in three-dimensional space by means of three coordinates. This is the process previously described for positioning and orienting instruments, jigs and bones for surgical use. Three coordinate axes are given, each perpendicular to the other two at the origin, the point at which they cross. The instant inventor is a user of Kane's Dynamics. Thus, each body or massless frame that is defined is assigned three unit vectors (or relative axis), labeled as either the 1, 2 or 3 axis within a particular reference frame. Relative to these axes, the position of any point in three-dimensional space is given by an ordered triple of real numbers, each number giving the distance of that point from the origin measured along the given axis, which is equal to the distance of that point from the plane determined by the other two axes. The created three dimensional holographic images may be constructed using generators and/or other components purchased from companies within the "International Hologram Manufacturers Association" (www.ihma.org), specifically companies such as "The Hologram Company" (sales@thehologramcompany.co.uk) and "API Holographics" (www.apigroup.com). If one chooses to go this route, components and even full holographic projectors may be commercially purchased. Then, the holographic projector or holographic components are used with a digital device, instrumentation, and computer algorithms to create the images, as well as size, position, and orient the images into the proper location during surgery. Alternatively, a specialized holographic projector may be fabricated from commercially available components and ensuring that the resolution and quality of the holographic images is ideal for medical use. Similar to the two dimensional images, each light beam or point within the holographic image is defined with respect to the fixed Newtonian reference frame, defined on the light beam instrument. Unlike moving a two-dimensional image, two processes may be used to move the holographic image. Either each point could be defined and then redefined with respect to the origin in the Newtonian reference frame, or at least three points within the holographic image could be defined with respect to the Newtonian reference frame and then three relative axes with the holographic relative reference frame could be constructed and these axes could be oriented and positioned with respect to the Newtonian reference frame. Again, as the three-dimensional image is moved, the relative transformation matrix will be redefined. Once the three-dimensional image is positioned in place by the surgeon, the coordinates for this relative transformation matrix are locked in place and may be used at anytime during the surgery by the surgeon.

Figure 25:
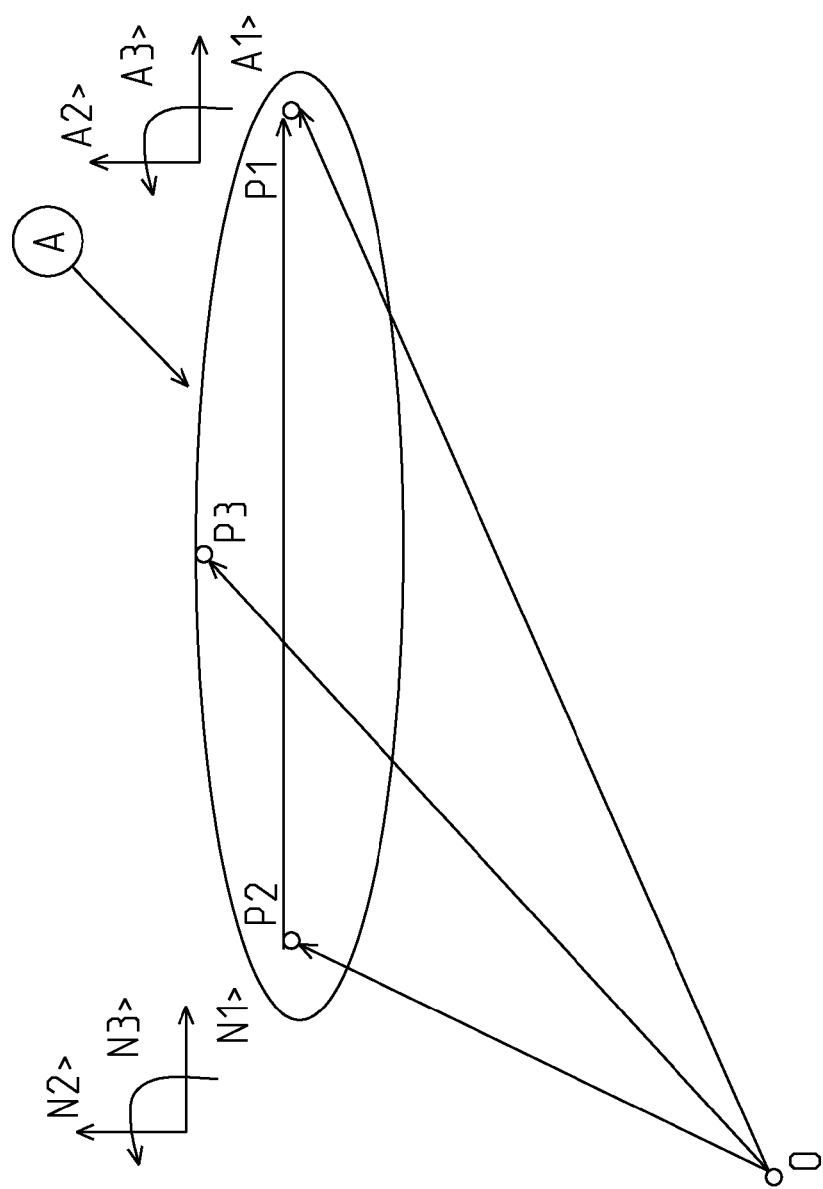
FIG. 25 is a diagram depicting a fixed point in the Newtonian reference frame with respect to three points of a three dimensional image.

Referring to FIG. 25, if three points are defined on the holographic image, one of these points must be defined out of the plane the first two points were defined within. Therefore, for this example, each of the three points is defined as P1, P2 and P2 on a three dimensional image taking the shape of an ellipse in any view or an elongated sphere. In this figure, the point O represents a fixed point in the Newtonian reference frame, within the light beam instrument or where the holographic image project is housed in the instrument. The image that is being projected is defined as body A and a relative reference frame with the unit vectors A1>, A2> and A3> are defined.

$$A1> = \frac{P\_P2\_P1>}{|P\_P2\_P1>|}$$

Unit vector A1> is defined by creating a line using the points P1 and P2 and the dividing this line by its magnitude. Next, the second unit vector is defined by cross multiplying vector A1> with the unit vector of the line between points P2 and P3 and dividing this function by its magnitude.

$$A2> = \frac{UnitVEC(P\_P2\_P3>) \times (A1>)}{|UnitVEC(P\_P2\_P3>) \times (A1>)|}$$

Figure 26:
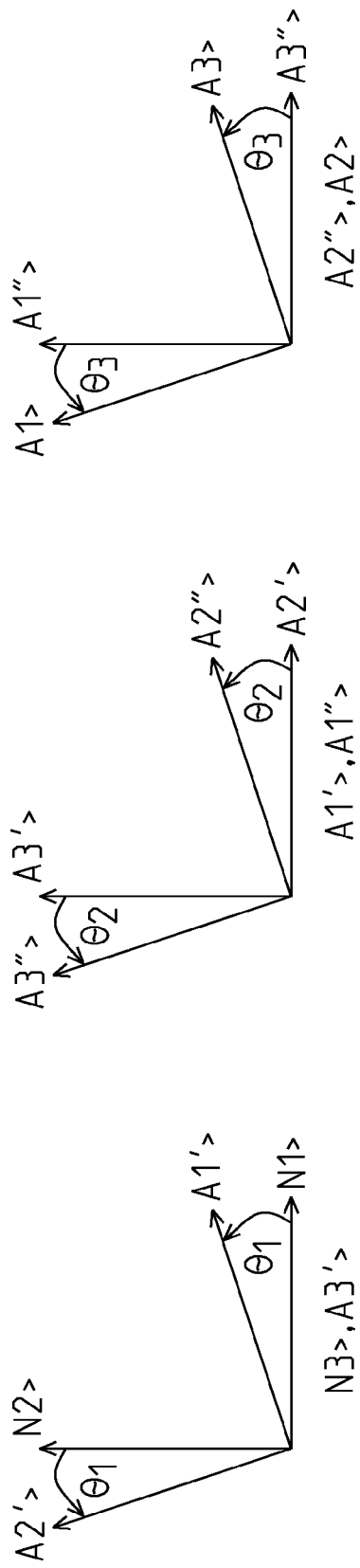
FIG. 26 are a series of diagrams showing how various vectors provide relative rotations of a three dimensional image with respect to a light beam instrument.

Finally, the third unit vector A3> is defined by cross multiplying A1> and A2>. Next, the transformation matrix can be derived using three successive rotations defined in FIG. 26, whereas the reference frame A represents a body, but the A' and A" reference frames are intermediate in nature and are defined as massless reference frames.

The sequential references frames could set up as follows:

$$\begin{Bmatrix} A1> \\ A2> \\ A3> \end{Bmatrix} = \begin{bmatrix} \cos(\theta 3) & 0 & -\sin(\theta 3) \\ 0 & 1 & 0 \\ \sin(\theta 3) & 0 & \cos(\theta 3) \end{bmatrix} \begin{bmatrix} 1 & 0 & 0 \\ 0 & \cos(\theta 2) & \sin(\theta 2) \\ 0 & -\sin(\theta 2) & \cos(\theta 2) \end{bmatrix} \begin{bmatrix} \cos(\theta 1) & \sin(\theta 1) & 0 \\ -\sin(\theta 1) & \cos(\theta 1) & 0 \\ 0 & 0 & 1 \end{bmatrix} \begin{Bmatrix} N1> \\ N2> \\ N3> \end{Bmatrix}$$

Then, using matrix multiplication, the following relative transformation between the Newtonian reference frame within the light beam instrument and the relative reference frame, the three dimensional image could be described as:

$$\begin{Bmatrix} A1> \\ A2> \\ A3> \end{Bmatrix} = \begin{bmatrix} (C\theta 1 \cdot C\theta 3 - S\theta 1 \cdot S\theta 2 \cdot S\theta 3) & (S\theta 1 \cdot C\theta 3 + S\theta 2 \cdot S\theta 3 \cdot C\theta 1) & (-S\theta 3 \cdot C\theta 2) \\ -(S\theta 1 \cdot C\theta 2) & (C\theta 1 \cdot C\theta 2) & (S\theta 2) \\ (S\theta 3 \cdot C\theta 1 + S\theta 1 \cdot S\theta 2 \cdot C\theta 3) & (S\theta 1 \cdot S\theta 3 - S\theta 2 \cdot C\theta 1 \cdot C\theta 3) & (C\theta 2 \cdot C\theta 3) \end{bmatrix} \begin{Bmatrix} N1> \\ N2> \\ N3> \end{Bmatrix}$$

In the transformation matrix listed above, θ1, θ2 and θ3 represent relative rotations of the three dimensional image with respect to the light beam instrument and as these angles changes, so does the three dimensional image. These angles may be previously defined before surgery, may equate to temporal or depended functions or may be changed intraoperatively either using dials and/or levers, audibly or through another measurement device. If the surgeon chooses to move the three points P1, P2 and P3 to navigate the three-dimensional image and would like to know the orientation of the image, more specifically θ1, θ2 and θ3, these angles may be mathematically derived using the following set of equations:

$$PA11 = C\theta1 \cdot C\theta3 - S\theta1 \cdot S\theta2 \cdot S\theta3$$

$$PA12 = S\theta1 \cdot C\theta3 + S\theta2 \cdot S\theta3 \cdot C\theta1$$

$$PA13 = -S\theta3 \cdot C\theta2$$

$$PA21 = S\theta1 \cdot C\theta2$$

$$PA22 = C\theta1 \cdot C\theta2$$

$$PA23 = S\theta2$$

$$PA31 = S\theta3 \cdot C\theta1 + S\theta1 \cdot S\theta2 \cdot C\theta3$$

$$PA32 = S\theta1 \cdot S\theta3 - S\theta2 \cdot C\theta1 \cdot C\theta3$$

$$PA33 = C\theta2 \cdot C\theta3$$

The foregoing nine equations represent an over determinant system, meaning you have too many equations for only three unknown quantities. The three angles of questions can also be derived using the following three equations:

$$\theta2 = \operatorname{Sin}^{-1}(PA23)$$

$$\theta3 = \operatorname{Cos}^{-1}(PA33/\operatorname{COS}(\theta2))$$

$$\theta1 = \operatorname{Cos}-1(PA22/\operatorname{Cos}(\theta3))$$

Although the use of three-dimensional images as disclosed herein references holographic or non-holographic images, these images could quite easily be constructed using any technique for defining and creating three-dimensional images. Also, the application for three dimensional images is disclosed in the context of total hip arthroplasty, however, those skilled in the art should understand that these three dimensional images and associated equipment could also be used for any joint, organ or structure within the human and animal body and could be used for other surgeries besides just total joint surgeries.

Figure 19:
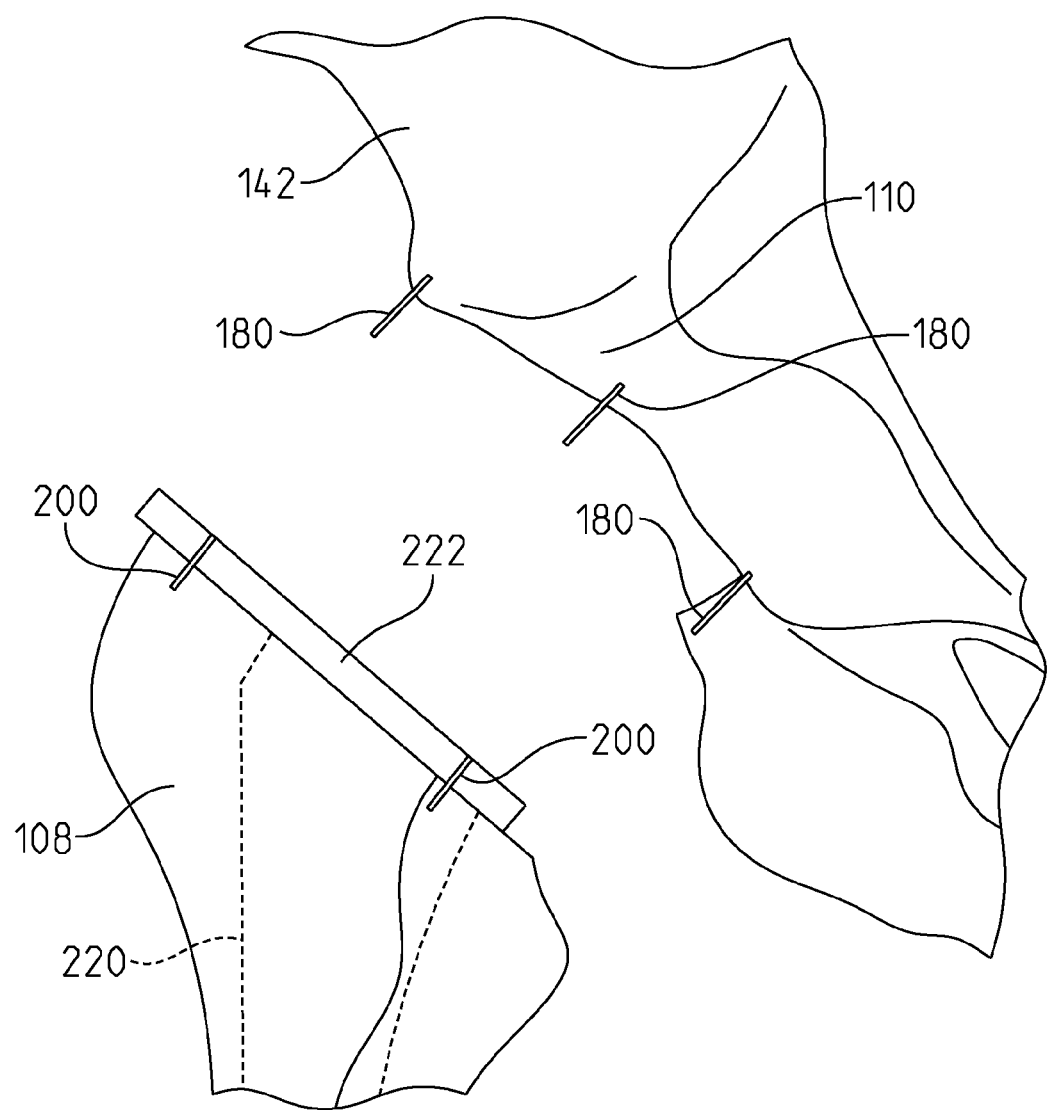
FIG. 19 is a magnified view, from the front, of the human hip joint area after acetabular reaming, proximal femoral bone removal, and insertion of a femoral stem.
Figure 20:
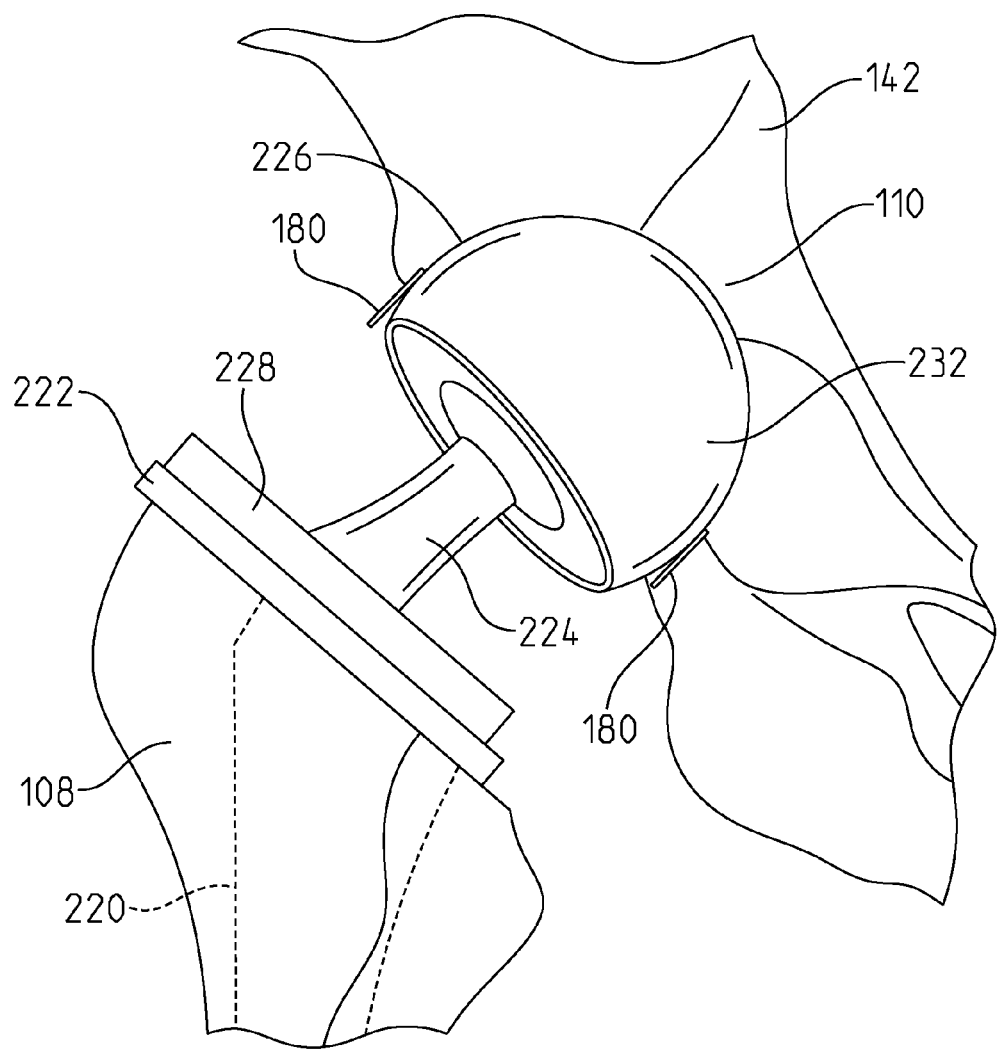
FIG. 20 is a magnified view, from the front, of the human hip joint area of FIG. 18 after attachment of the acetabular components, femoral neck, and femoral ball.

Referencing FIGS. 19 and 20, after the distal femur has been cut, the final femoral and acetabular implants are mounted to the pelvis 142 and the femur 108. Mounting of the final femoral implants may utilize the guide pins 200 or virtual instrumentation through the use of the light beam source instrument. For example, presuming any prefatory reaming of the intramedullary canal of the femur has taken place (and this reaming can also utilize the guide pins 200 for alignment), the final implanted femoral stem 220 is inserted into the intramedullary canal of the femur 108 using the guide pins 200. Presuming the final femoral implant is modular, the final femoral neck 224 and femoral ball 226 are mounted to the implanted femoral stem 220. In this exemplary embodiment, the femoral stem 220 includes an endplate 222 that sits upon the outer proximal surface of the femur 108. In addition, the femoral neck 224 also includes an endplate 228 that couples to the endplate 222 of the femoral stem to mount the neck to the stem.

In this exemplary embodiment, the femoral stem 220 is offset from the femoral neck 224. While an offset between the stem 220 and neck 224 may occur infrequently, it has been shown to document the ability to reposition the neck independent from the stem and the modularity of this exemplary implant. In some cases, however, the final implant will be integrated or a single piece so that variable orientation and position of the stem 220 with respect to the neck 224 is not possible.

It should also be noted that the final acetabular implants may be mounted to the pelvis 142 utilizing the guide pins 180. For example, presuming all prefatory reaming of the acetabulum is complete (and this reaming can also utilize the guide pins 200 for alignment), the final implanted acetabular cup and cup insert 232 are inserted into the reamed acetabulum 110 using the guide pins 180. Presuming the final acetabular cup and cup inserts are modular, minor modifications can be made to the orientation and position of each component with respect to the other. After both the final femoral and acetabular components are implanted and secured, the femoral ball 226 is seated into the acetabular cup insert 232.

Figure 21:
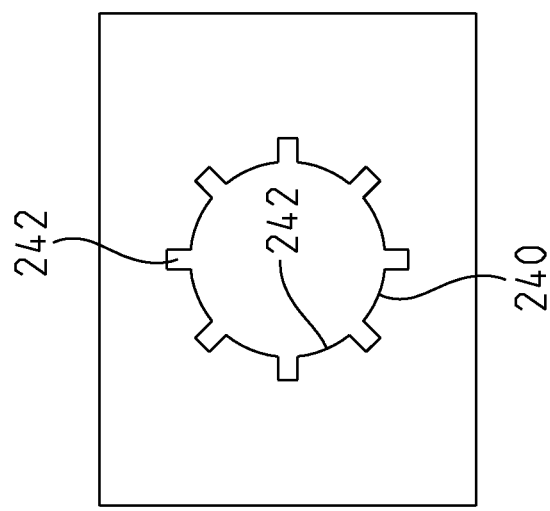
FIG. 21 includes a profile and overhead view of a proximal femur showing insertion of an exemplary femoral sleeve.
Figure 21:
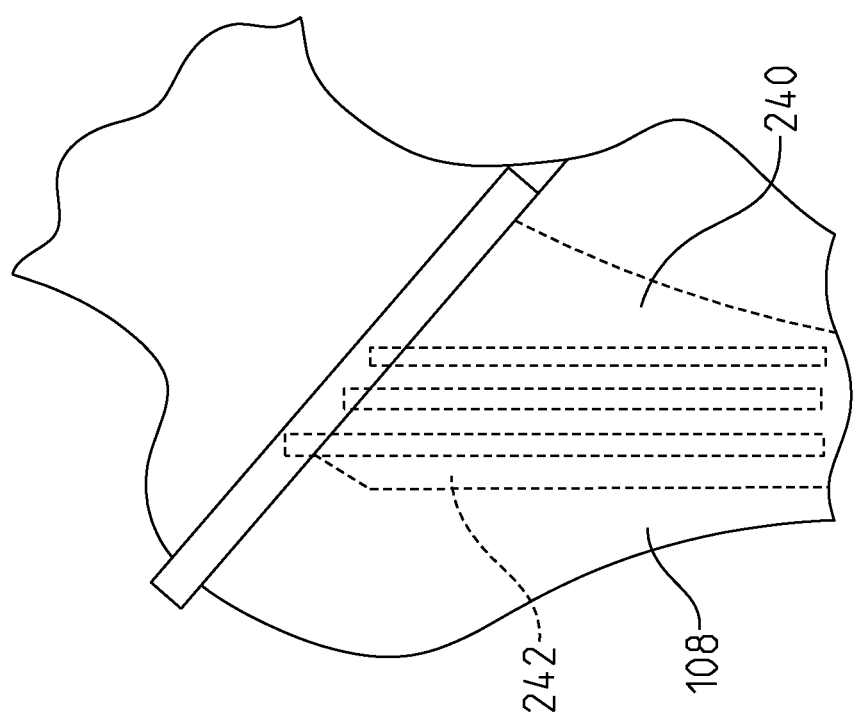

Referring to FIG. 21, it is also within the scope of the invention to include a femoral sleeve 240 for insertion into the intramedullary canal of the femur 108. The exemplary sleeve 240 may be either press fit into the femur 108 or cemented. In contrast, current techniques commonly cement or press fit the femoral implant into the femur 108. Once this femoral stem is secured to the bone using this preexisting technique, removal for revision surgery is very difficult. The instant invention introduces a modular type femoral stem that slides into the femoral sleeve 240. This femoral sleeve 240 may be designed with internal grooves and projections 242 so that a femoral stem 220 (see FIG. 19) may be inserted into the sleeve at multiple angles. The sleeve could also be smooth without grooves. If grooves are used, these grooves and projections 242 may alternate or include a pattern that coincides with a pattern on the femoral stem 220 to ensure proper orientation of the femoral stem with respect to the sleeve. The implanted femoral stem 220 is locked into place within the sleeve 240. By using a sleeve 240 to interpose the femur 108 and the femoral stem 220, it provides the advantage that if the femoral stem needs to be removed for any reason, the femoral stem can be unlocked from the sleeve and then removed without causing additional damage to the intramedullary canal. Thereafter, a new or revised femoral stem may be inserted into the sleeve 240. Accordingly, the use of a permanent sleeve 240 ensures that initial femoral stem alignment is maintained in any femoral version surgery. Also, if for some reason it is deemed that the femoral stem orientation is not proper for that patient, rather than having to remove the femoral stem from the femur, the femoral implant in this in this patient may be removed and then the version angle may be changed and thereafter the femoral stem is re-positioned back into the sleeve.

While the foregoing sleeve 240 has been described as having a fixed orientation and position with respect to the femur 108, it is also within the scope of the invention for the sleeve 240 to include mobile bearing functionality. This functionality may be the result of a pair of sleeves that are telescopic, with the inner (smaller diameter) sleeve including the internal grooves and projections 242. This structure allows the inner sleeve to rotate with respect to the femur 108 and may be limited to retard a fully 360 degrees of femoral stem rotation.

Another exemplary alternative includes a sleeve that has no internal grooves and does contain a locking mechanism. The sleeve may be cemented and/or press fit into the femur. The femoral stem is of a round or oval shape and free to rotate within the sleeve. The femoral stem may be locked in one direction so that it can be removed from the sleeve, but is free to rotate around its longitudinal axis or any defined axis that is necessary to maintain concentric spheres.

Figure 22:
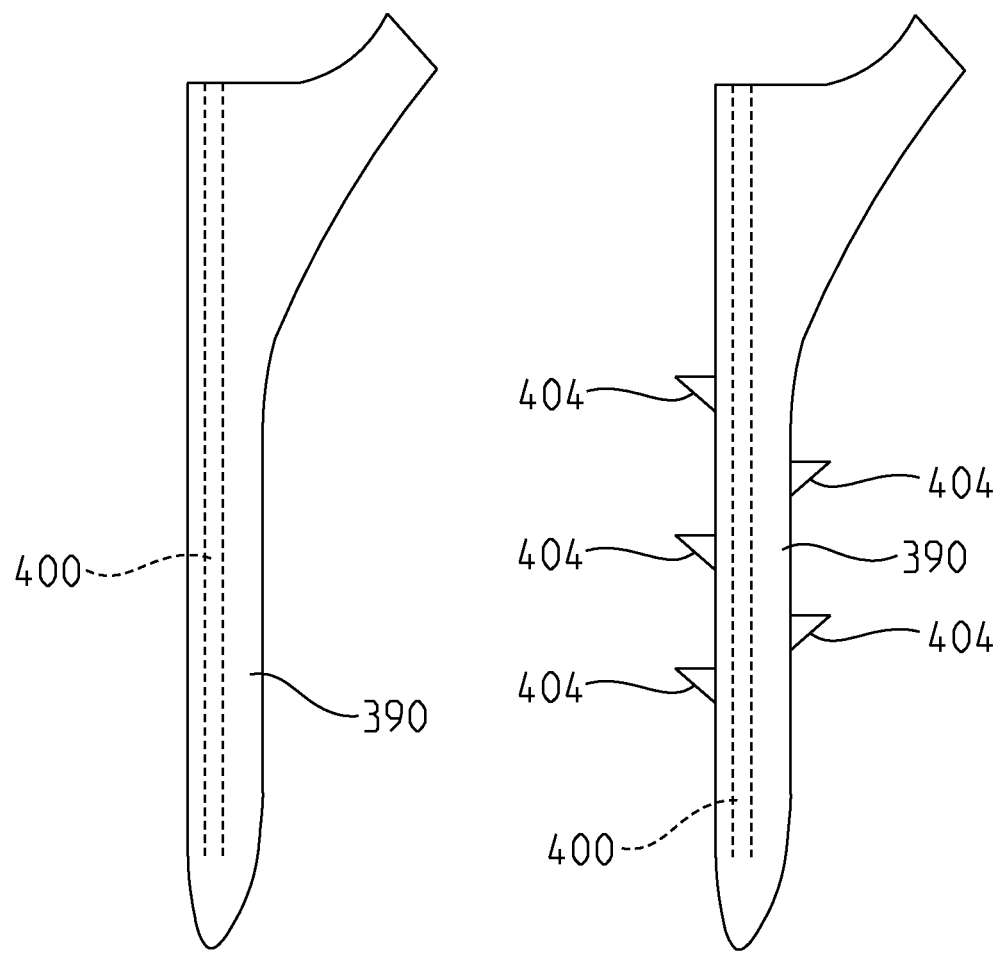
FIG. 22 comprises profile views of an exemplary femoral stem in accordance with the instant invention when the elements are deployed or retracted based upon the position of the screw.
Figure 23:
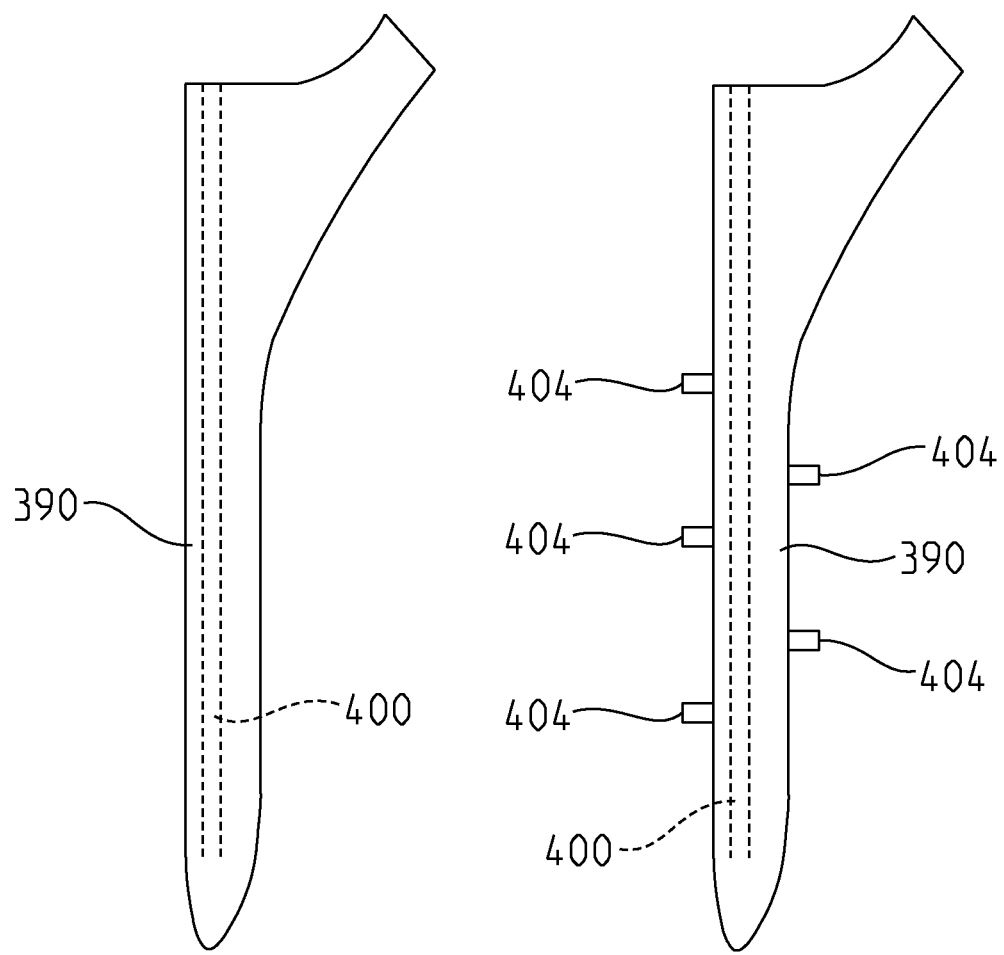
FIG. 23 comprises profile views of an exemplary femoral stem in accordance with the instant invention when the elements are deployed or retracted based upon the position of the screw.

Referring to FIGS. 22 and 23, in another exemplary embodiment, the femoral stem 390 has an internal longitudinal screw (or gear mechanism) 400. After the femoral stem 390 is implanted into the femur, the surgeon can turn the screw 400 on the superior aspect of the femoral stem, which will force elements 404 to protrude from the stem into the bone, leading to greater fixation of the femoral stem to the bone. If for some reason the implant needs to be removed during revision surgery, the surgeon can turn the screw 400 in the opposite direction, which operates to pull the elements 404 back into the stem 390 allowing for the stem to be more easily removed. If the femoral stem is to be inserted into the femoral sleeve 240 (see FIG. 21), the surgeon turns the screw 400 to reposition the elements 404 to protrude away from the stem into grooves 242 in the sleeve. In exemplary form, the elements 404 may take on various shapes and sizes and be located at various positions along the femoral stem and/or sleeve 240. For example, the elements 404 take on a triangular profile in FIG. 22, while the elements take on a rectangular profile in FIG. 23.

It should be noted that the femoral stem and femoral sleeve may take on any number of shapes both on the interior and exterior. For instance, the inside of the femoral sleeve may be elliptical, while the exterior of the femoral stem is rectangular. Likewise, the exterior of the femoral sleeve may be rectangular, elliptical, or any other cross-section.

Following from the above description and invention summaries, it should be apparent to those of ordinary skill in the art that, while the methods and apparatuses herein described constitute exemplary embodiments of the present invention, the invention is not limited to the foregoing and changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A trial for use with total hip arthroplasty, the trial comprising:
a first spherical insert having a plurality of tabs mounted thereto, each of the plurality of tabs at least partially defining an orifice, wherein the first spherical insert is sized to fit within an unreamed acetabulum, the first spherical insert further being sized to contact the acetabulum and a resected femoral neck when the first spherical insert is positioned within the unreamed acetabulum.

2. The trial of claim 1, wherein the first spherical insert includes a first semispherical half and a second semispherical half that engage and disengage one another.

3. The trial of claim 2, wherein the first semispherical half engages the second semispherical half along an equator of the first spherical insert.

4. The trial of claim 3, wherein the plurality of tabs extend outwardly from the first semispherical half adjacent to the equator.

5. The trial of claim 1, wherein the orifice of each of the plurality of tabs is sized to receive a pin.

6. A surgical instrument for use in a hip arthroplasty, the surgical instrument comprising:
a body including a first piece removably coupled to a second piece, each of the first piece and the second piece having a convex curved outer surface, and
a plurality of tabs extending outward from the body, each tab having an orifice defined therein that is sized to receive a pin, wherein the body is sized to fit within an unreamed acetabulum, the body further being sized to contact the acetabulum and a resected femoral neck when the body is positioned within the unreamed acetabulum,
wherein the convex curved outer surfaces of the first piece and the second piece define a sphere when the first piece is coupled to the second piece.

7. The surgical instrument of claim 6, wherein each tab of the plurality of tabs extends outwardly from the first section of the spherical outer surface and the second piece is devoid of any of the plurality of tabs.

8. A surgical instrument for use in a hip arthroplasty, the surgical instrument comprising:
a body having an outer surface that defines a sphere, and
a plurality of tabs extending radially outward from the outer surface, each tab having an orifice defined therein that is sized to receive a pin, wherein the outer surface of the body is sized to fit within an unreamed acetabulum, and the outer surface of the body further being sized to contact the acetabulum and a resected femoral neck when the body is positioned within the unreamed acetabulum.

9. The surgical instrument of claim 8, wherein the body includes (i) a first piece and (ii) a second piece removably attached to the first piece at a circular edge of the first piece.

10. The surgical instrument of claim 9, wherein the plurality of tabs extend radially outward from the first piece at the circular edge.

* * * * *